United States Patent [19]

Premuzic et al.

[11] Patent Number: 5,297,625
[45] Date of Patent: Mar. 29, 1994

[54] BIOCHEMICALLY ENHANCED OIL RECOVERY AND OIL TREATMENT

[75] Inventors: Eugene T. Premuzic, East Moriches; Mow Lin, Rocky Point, both of N.Y.

[73] Assignee: Associated Universities, Inc., Washington, D.C.

[21] Appl. No.: 905,391

[22] Filed: Jun. 29, 1992

Related U.S. Application Data

[63] Continuation-in-part of Ser. No. 571,917, Aug. 24, 1990, abandoned.

[51] Int. Cl.$^5$ .............................................. E21B 43/22
[52] U.S. Cl. .................................... 166/246; 166/274; 435/245
[58] Field of Search ..................... 166/246, 273, 274; 435/9, 245

[56] References Cited

U.S. PATENT DOCUMENTS

| | | | |
|---|---|---|---|
| 3,332,497 | 7/1967 | Jones | 166/246 |
| 3,340,930 | 9/1967 | Hitzman | 166/246 |
| 4,450,908 | 5/1984 | Hitzman | 166/246 |
| 4,640,767 | 2/1987 | Zajic et al. | 166/246 X |
| 4,780,238 | 10/1988 | Premuzic | 252/184 |
| 4,905,761 | 3/1990 | Bryant | 166/246 |
| 5,002,888 | 3/1991 | Kilbane, II | 435/252.31 |
| 5,163,510 | 11/1992 | Sunde | 166/246 |

FOREIGN PATENT DOCUMENTS 140067 2/1980 Fed. Rep. of Germany ...... 166/246

Primary Examiner—George A. Suchfield
Attorney, Agent, or Firm—Margaret C. Bogosian

[57] ABSTRACT

This invention relates to the preparation of new, modified organisms, through challenge growth processes, that are viable in the extreme temperature, pressure and pH conditions and salt concentrations of an oil reservoir and that are suitable for use in microbial enhanced oil recovery. The modified microorganisms of the present invention are used to enhance oil recovery and remove sulfur compounds and metals from the crude oil.

5 Claims, 28 Drawing Sheets

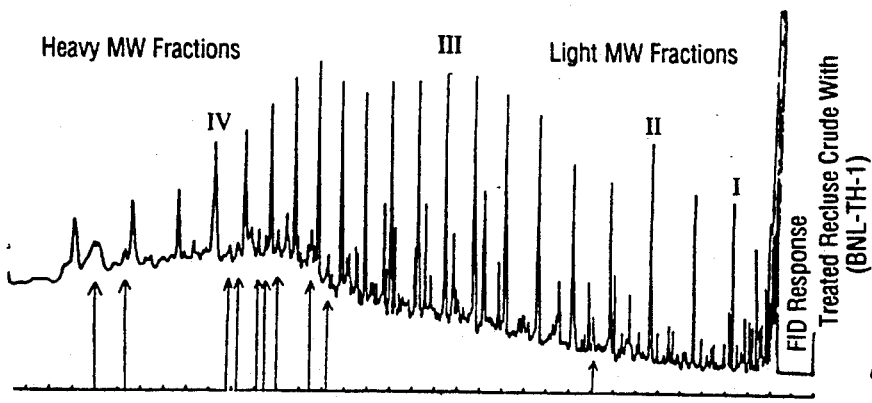
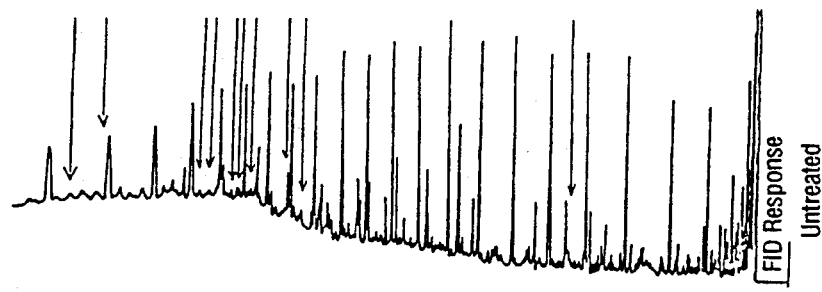
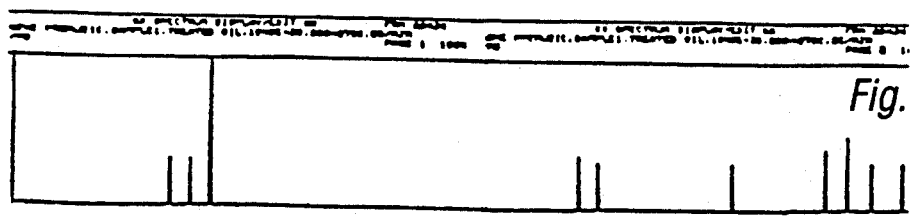
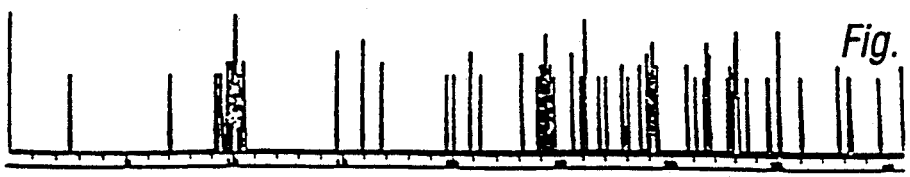
Crude oil (Recluse Wyoming) treated with BNL-TH-1 at 70°C and 2000C psi GC-MS scan for M/e 32 signals; (a) untreated (b) treated oil.

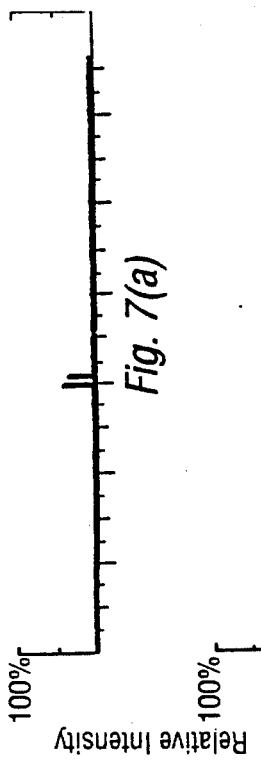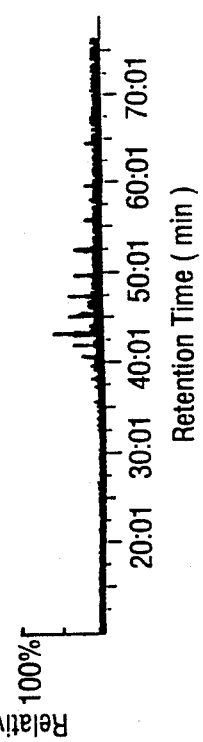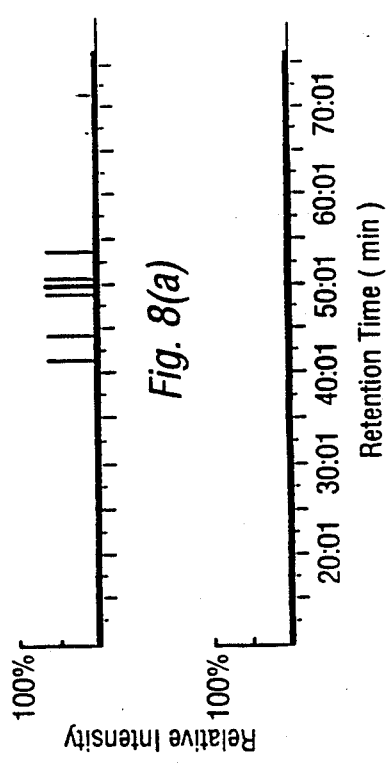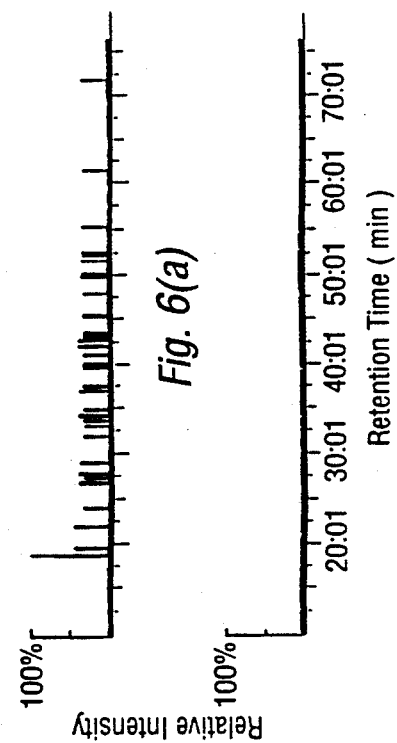
Fig. 5(a)
Fig. 5(b)
Fig. 6(a)
Fig. 6(b)
Fig. 7(a)
Fig. 7(b)
Fig. 8(a)
Fig. 8(b)

HPLC Trace Of PR3 + BNL-4-22 + medium
8.10 lactic, 11.58 propionic, 13.10 isobutyric, 23.87 n-butanol

FPD TRACE OF BOSCAN CRUDE OIL: BEFORE TREATMENT WITH BNL-4-22.

FPD TRACE OF BOSCAN CRUDE OIL: AFTER TREATMENT WITH BNL-4-22.

GAS CHROMATOGRAPHY-FLAME PHOTOMETRIC DETECTOR (GCFPD) TRACE (SULFER EMISSION INTENSITY) OF UNTREATED WILMINGTON, CA, CRUDE BIOTREATED WITH BNL-4-21.

MOLECULAR MARKERS:

C: PHENYL SULFIDE
D: DIBENZOTHIOPHENE
E: C-1 DIBENZOTHIOPHENE

GAS CHROMATOGRAPHY-FLAME PHOTOMETRIC DETECTOR (GCFPD) TRACE (SULFER EMISSION INTENSITY) OF UNTREATED WILMINGTON, CA, CRUDE PRE-EMULSIFIED WITH 1.0% TERGITOL AND BIOTREATED WITH BNL-4-24.

GAS CHROMATOGRAPHY-FLAME PHOTOMETRIC DETECTOR (GCFPD) TRACE (SULFER EMISSION INTENSITY) OF UNTREATED WILMINGTON, CA, CRUDE PRE-EMULSIFIED WITH 0.5% TERGITOL AND BIOTREATED WITH BNL-4-24.

BIOCHEMICALLY ENHANCED OIL RECOVERY AND OIL TREATMENT

This invention was made with Government support under contract number DE-AC02-76CH00016, between the U.S. Department of Energy and Associated Universities, Inc. The Government has certain rights in the invention.

RELATED APPLICATIONS

The instant application is a continuation-in-part of co-pending application Ser. No. 571,917 filed Aug. 24, 1990 in the names of Eugene T. Premuzic and Mow Lin entitled "Microbial Enhanced Recovery of Oil".

BACKGROUND OF THE INVENTION

1. Field of the Invention

This invention relates to microbially enhanced recovery of oil at elevated temperatures and pressures. More particularly, this invention relates to the selection, isolation and use of aerobic and anaerobic microorganisms, preferably thermophilic microorganisms, which can be maintained at elevated temperatures, pressures, salinity and pH extremes using crude oil and other indigenous matter as a source of energy, perhaps their sole source of energy, for enhanced oil recovery.

2. Background of the Related Art

Oil bearing geological formations often yield crude oil in response to naturally occurring forces, such as gas pressure, gravitational pressure due to the surrounding rock or hydraulic pressure from ground water or steam. The pressure forces the crude oil from the geological formation through a fissure or well at the surface. To increase the recovery of crude oil, pumping is employed. When the level of the oil drops, however, pumping becomes unproductive. In these cases, secondary recovery methods, such as gas, drive or water flooding are utilized to raise the levels of crude oil in the reservoirs.

To facilitate an increase in the yields from these secondary recovery methods, it has long been proposed to subject the geological oil bearing formation to the action of oil-releasing bacteria. This bacterial treatment, called microbial enhanced oil recovery ("MEOR") would be used to supplement the aforementioned secondary recovery methods. The major obstacle that has prevented the implementation of MEOR has been the difficulty in finding, isolating or engineering microorganisms which can survive the harsh variety of environmental conditions present in oil reservoirs. These conditions include temperatures which range from approximately 49° to 90° C., a pH range from approximately 2 to 10, and large variations in brine concentrations, mostly potassium or sodium chloride with average percent total solids ranging from 1.3 to 15.6, as reported by McInerney during the *International Conference On Microbial Enhancement Of Oil Recovery*, May 16–21, 1982, Bartlesville Energy Technology Center, Bartlesville, Okla. (1983). McInerney observed that magnesium and iron are usually present in most reservoirs at concentrations sufficient to support microbial growth; that sulfur, nitrate and phosphate are not usually present in sufficient concentrations to support microbial growth; and that oxygen concentration are low, indicating anaerobic conditions. McInerney further noted that although different microorganisms grow and reproduce under certain reservoir conditions, for example temperatures from 0° to 100° C., pH from 1 to 10, salinity from 0 to 35%, and pressures up to 1,000 atmospheres, each particular species could only grow at a particular narrow range of conditions. Microorganisms that are naturally present in the reservoir also usually act on the oil to produce undesirable products such as hydrogen sulfide, which are not beneficial to oil recovery.

Microorganisms can be classified in terms of temperature ranges that permit viability. Psychrophiles designate microbial species which grow at a temperature range of from −5° to 22° C.; mesophiles grow from 10° to 45° C.; and thermophiles grow between 40° and 80° C., or higher for extreme thermophiles; see Ljungdahl, "Physiology of Thermophilic Bacteria", *Adv. Microbial. Physiol.*, 19 149-243 (1979). Similar classifications have been used for the growth of microbial species due to pressure [see Marquis et al., "Microbial Life Under Pressure", in Microbial Life in *Extreme Environment*, Kushner (ed.), 105-159, Academic Press, N.Y., N.Y. (1978) and Marquis, et al., "Microbial Barobiology", *Bioscience*, 32, 267-271 (1982)]; pH [see, Langworthy "Microbial Life In Extreme pH Values", *Microbial Life in Extreme Environments*, Kushner (ed.), 279-317, Academic Press, N.Y., N.Y. (1978)]; and due to salt concentrations [see Kushner, "Life in High Salt and Solute Concentrations: Halophilic Bacteria", *Microbial Life in Extreme Environments*, Kushner (ed.), 313-368, Academic Press, N.Y., N.Y. (1978)]. While some of the microorganisms described by McInerney referenced above are tolerant to individual environmental effects, none of these microorganisms could withstand the combination of high temperatures and high pressures sometimes rising to over 2,000 psi which are commonly encountered in oil reservoirs.

In the past several years, various university research groups, the National Institution for Petroleum Research, and a number of research groups abroad have laid the ground work for MEOR. See, King and Stevens (Eds), *Proc. of the First International MEOR Workshop*, Apr. 1-3, 1986, DOE/BC/10852-1 (1986), especially the Lazar article at pages 124-151 of these proceedings, which indicated that MEOR was a promising technology. The conclusion at these workshops was that considerably more research was needed because most field tests were either inconclusive or proved to be outright failures.

An understanding the chemistry, biochemistry and biogeochemistry of interactions between microorganisms, oils and sedimentary matrices in which these oil deposits occur has been somewhat lacking. Many of the bacteria which have been studied were not tested in the laboratory under reservoir conditions. Nevertheless, the available data suggests several mechanisms for microorganisms to function in MEOR biotechnology. See, Bryant and Douglas, *IITRI/NIPER*, 449-456, SPE 16284, Society of Petroleum Engineers (1987). These mechanisms include: (1) production of gases ($CO_2$, $H_2$, and $CH_4$) which can increase pressure in the reservoir and reduce oil viscosity; (2) microbial production of low molecular weight acids, which cause rock solubilization; (3) production of biosurfactants which decrease surface and interfacial tensions; (4) microbially mediated changes in wettability; and, (5) production of polymers which facilitate mobility.

It was suggested by Grula in *Proc. of The First International MEOR Workshop, Apr. 1-3, 1986*, 152-213, DOE/BC/10852-1 (1986) that some of the desirable properties of bacteria to be used in MEOR should include the capacity for large productions of "oil releasing" metabolites (e.g., low molecular weight alcohols, acids, surfactants and gases). These microorganisms should not require expensive nutrients, should be able to survive under anaerobic conditions, and should be capable of withstanding relatively high pressures, temperatures, pH variations and salinaties. Additionally, these microorganisms should be easily grown in facilities above ground, remain viable over extended periods of time and be easily transportable. Once placed in the reservoir, these microorganisms should continue to be viable under extreme conditions, and continue their activity upon refeeding. It is to be understood that all of the requirements may not be met by a single type/strain of microorganism and that mixed type/strains may be appropriate for MEOR.

Under certain reservoir conditions, a number of microorganisms have been found to be present in formation waters [see Lazar (1986) supra]. According to Lazar, the usefulness of these bacteria appeared to be limited, since these organisms can only grow in reservoirs of a given depth, salinity, temperature and permeability range. Also, the growth of these bacteria is limited by increases in the concentration of products generated by their own metabolism.

Known thermophilic organisms live under harsh conditions, such as low pH (approximately about $\leq 1-3$) and high temperatures (up to 110° C.); some are also known to grow under alkaline conditions; [see Brock, *Life at High Temperatures*, Science 20, 132–138 (1985), and *Thermophilic Microorganisms and Life at High Temperatures*, 465 pp, Springer Veralag, New York, N.Y. (1978)]. These organisms can use inorganic and organic energy sources (e.g., sulfides, elemental sulfur and ferrous ions). Some of these bacteria are also capable of switching from aerobic to anaerobic metabolism. Further, the natural habitats of these organisms are geothermal brines which allow them to tolerate high salt concentrations. Accordingly, the general properties of thermophilic organisms, although not fully explored, have indicated that they possess a number of the desirable properties for MEOR outlined during the 1986 Workshop, and further verified in recent status reports [see, King, *MEOR Technical Status and Assessments Of Needs*, DOE/BC/10852-2, DE7-0001227 (1987), and Jenneman, "The Potential for in situ Microbial Applications", *Microbial Enhanced Oil Recovery, Developments In Petroleum Science*, 22, Donaldson, et al. (eds.), 37–74, Elsevier, New York, N.Y. (1989)].

The use of thermophilic microorganisms to break down complex hydrocarbons in the laboratory environment, has been disclosed in the patent literature. For example, U.S. Pat. No. 2,413,278 to Zobell, discloses the use of bacteria from the genus Desulfovibrio. Some species of this bacteria are disclosed as being active in a temperature range from 70° F. and 180° F. (21.1° C. to 82.4° C.). These bacteria are strict anaerobes, and are inhibited by H+ ion concentrations lower than pH 6.0. Additionally, there is no disclosure that these microorganisms are functional at anything but ambient pressures. Similarly, in U.S. Pat. No. 2,660,550 to Updegraff et al., the same thermophilic bacteria described in the Zobell patent are used, the improvement being the introduction of molasses in the well water as a source of nutrients and minerals. As in Zobell, the bacteria although described as highly thermophilic, were not tested for growth under high pressures and aerobic conditions.

Additionally, U.S. Pat. No. 2,975,835 to Bond, describes the use of the same bacteria from the genus Desulfovibrio as described above. Bond also discloses the use of other bacteria such as *Asperillus flavus*, *Bacillus methanicus* and *Bacillus ethanicus* in suitable growth medium. The growth medium containing the bacteria is combined with an aqueous gelling agent and injected under pressure into a well, in order to fracture low permeability oil bearing rock formations. The pressure applied is described as from 0.6 to 1 p.s.i. for each foot of overburden, i.e. for each foot measured from the surface to the formation to be fractured. In an example, a pressure of 900 p.s.i. is applied to fracture the rock. After fracturing, the pressure immediately drops to near ambient pressure. This type of sudden pressure reduction often inactivates the bacteria. Also, the bacteria disclosed by Bond are not described as being capable of growing at high pressures. They are only able to survive in the gel under relatively low pressures (usually less than 1000 p.s.i.) applied for short periods of time until the rock is fractured. Additionally, Bond teaches to maintain the temperature of the gel under 130° F. to avoid destroying the bacteria.

A bacterium useful for cleaving C-S bonds for sulfur removal from dibenzothiophene, resulting in substantially sole products of inorganic sulfate in 2-hydroxybiphenyl is described in U.S. Pat. No. 5,002,888 to Kilbane, II. The preferred microorganism is identified as *Bacillus sphaericus* ATCC# 53969. The patent describes this bacteria as being able to metabolize the C-S bonds at temperatures from about 20° to 34° C. Accordingly, it appears that this microorganism and method cannot be used in the high pressure and high temperature environment existing in oil reservoirs.

Accordingly, a method for preparing, isolating and utilizing a microorganism which can metabolize crude oils and other high molecular weight hydrocarbons as a source of energy, simultaneously metabolize and solubilize sulfur and organometallic compounds in the crude oils, and emulsify heavy crudes under the extreme conditions existing in oil reservoirs, including temperatures of up to 70°–85° C., high pressures of up to about 200–2,500 p.s.i., high salinities and extreme pH variations, has not previously been provided.

SUMMARY OF THE INVENTION

Accordingly, these goals and objectives have been met by the present invention which provides a method of preparing microorganisms suitable for use in microbially enhanced oil recovery (MEOR). The modified bacteria of the present invention can withstand reservoir conditions of extreme pH, temperatures up to 70°–85° C. and pressures of over 2000 to 2500 p.s.i. The method of the present invention includes the use of a challenge growth process which affects the adaptation of strains of microorganism to the pH and pressure conditions of an oil reservoir environment by selecting several microorganism strains having properties which may be useful for MEOR. The challenge growth process is a controlled strategy for the production of a mutant particularly useful in the treatment of crude oil. These strains are initially grown in a medium containing crude oil supplemented with other sources of nutrients, such as minerals and more easily metabolized sources of energy such as molasses and yeast extract. The strains that survive in the presence of crude oil are then subjected to further challenge by selection under more extreme conditions. The selection process proceeds by the removal of more easily metabolizable carbon sources while stepwise increasing the temperature, pressure, salinity and varying of the pH. The resulting modified thermophilic bacteria exhibit different chemical and biochemical properties than the bacterial strains subject to the challenge growth process. These chemical and biochemical properties have been used, following common microbiological methods, to identify the resulting unique and novel modified thermophilic bacteria. Modified thermophilic bacteria produced by the challenge growth process according to the present invention include modified *Achromobacter* sp. BNL-4-23 (ATCC 55021), *Sulfalobus solfataricus* BNL-TH-29 (ATCC 55022), *Sulfalobus solfataricus* BNL-TH-31 (ATCC 55023), *Pseudomonas* sp. BNL-4-24 (ATCC 55024), *Leptosoirillum ferrooxidans* BNL-5-30 (ATCC 53992), *Leptospirillum ferrooxidans* BNL-5-31 (ATCC 53993), *Acinetobacter calcoaceticus* BNL-4-21 (ATCC 53996), *Arthrobacter* sp. BNL-4-22 (ATCC 53997), and/or mixtures thereof.

Accordingly, the present invention also provides a process for the recovery of oil from an underground oil-bearing reservoir. The process includes injecting an aqueous solution containing the modified microorganisms or a mixture of microorganisms modified through the challenge growth process, to be suitable for use in oil recovery and grown to their maximum strength and maturity, into the reservoir. Subsequent to allowing the modified microorganism to act on the oil in the reservoir, the emulsified/modified oil is removed from the reservoir by conventional methods. This process can be conducted in conjunction with conventional and enhanced oil recovery technology such as water flooding or other technologies. By adapting the modified microorganisms for MEOR under the extreme reservoir conditions, the process of the present invention produces oils that are emulsified, acidified, have a qualitative and quantitative change in light and heavy fractions of the crudes, are chemically changed in the fractions containing sulfur compounds and contain less trace metals such as nickel and vanadium which are solubilized by the microorganisms. These physical and chemical changes are dependent upon the particular modified microorganism species that is used. The process of the present invention can be enhanced by the use of the mixture of different microorganisms each having a desired property. Further enhancement of this process can be achieved by the introduction of an emulsifying agent into the oil bearing reservoir prior to or at the time of injection of the aqueous solution containing the microorganism or mixture of microorganisms.

For a better understanding of the present invention, reference is made to the following description and examples in conjunction with accompanying figures and tables, the scope of which is pointed out in the appended claims.

BRIEF DESCRIPTION OF THE DRAWINGS

FIG. 3 is a GC analysis of Recluse crude (a) untreated (b) treated with modified *Sulfalobus acidocaldarious* species (BNL-TH-1) at 70° C. and 2000 p.s.i.

FIG. 4 is a GC-MS Scan for M/e 32 signals as markers of Recluse Crude: (a) untreated (b) treated with modified *Sulfalobus acidocaldarious* species (BNL-TH-1) at 70° C. and 2000 p.s.i.

FIG. 5 shows degradation of hydrocarbons, (a) before treatment and (b) after treatment, m/e 57 ion trace of PR3 crude treated with BNL-4-24.

FIG. 6 shows degradation of alkylarenes, (a) before treatment and (b) after treatment, m/e 91 ion trace of PR3 crude treated with BNL-4-24.

FIG. 7 shows degradation of aromatic hydrocarbons, (a) before treatment and (b) after treatment, m/e 169 ion trace of PR3 crude treated with BNL-4-24.

FIG. 8 shows degradation of cyclic hydrocarbons, (a) before treatment and (b) after treatment m/e 135 ion trace of PR3 crude treated with BNL-4-24.

DEPOSIT

Figure 1:
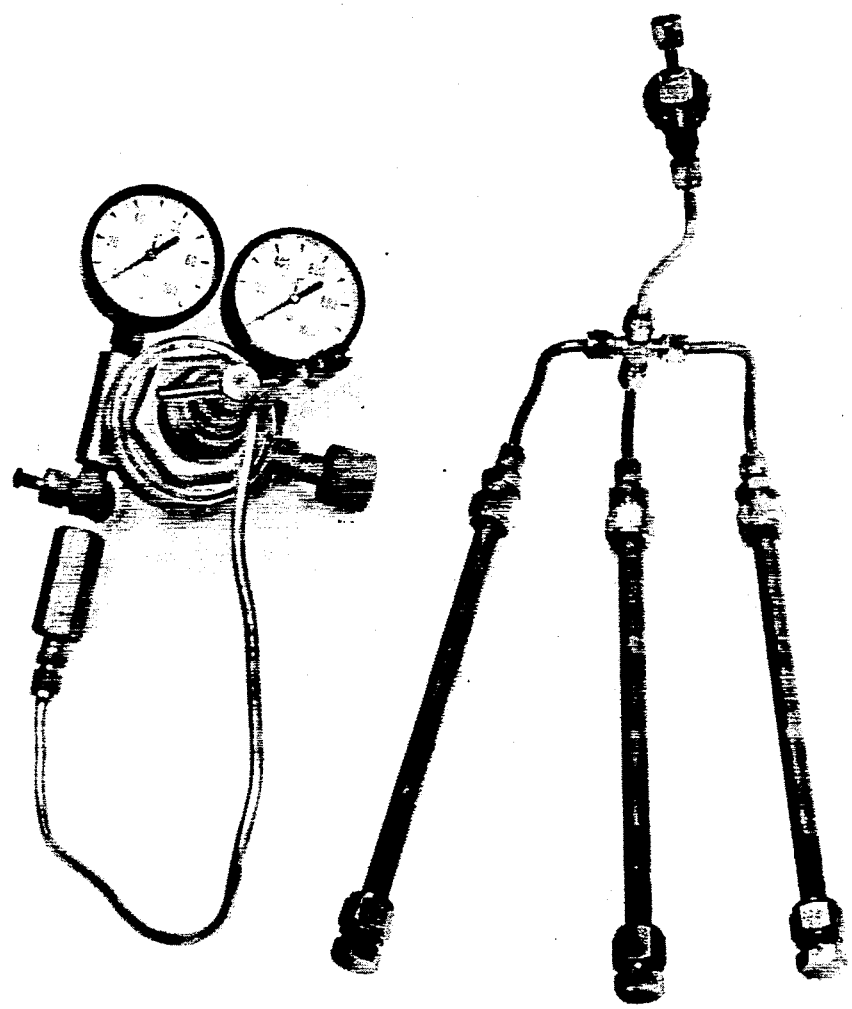
FIG. 1 is a photograph of the bioreactors and pressure regulator and gauges making up the apparatus for preparing the microorganisms of the present invention.

A number of microorganisms, modified following the procedures of the present invention and illustrative of the modified thermophilic microorganisms useful in the MEOR process of the present invention have been deposited in the American Type Culture Collection prior to the filing date of this application in accordance with the permanency and accessibility requirements of the U.S. Patent and Trademark Office. The following is a list of such deposited microorganisms:

| Scientific Description | Applicants' Reference | ATCC Designation |
| --- | --- | --- |
| Achromobacter sp. | BNL-4-23 | 55021 |
| *Sulfalobus solfataricus* | BNL-TH-29 | 55022 |
| *Sulfalobus solfataricus* | BNL-TH-31 | 55023 |
| Pseudomonas sp | BNL-4-24 | 55024 |
| *Leptospirillum ferrooxidans* | BNL-5-30 | 53992 |
| *Leptospirillum ferrooxidans* | BNL-5-31 | 53993 |
| *Acinetobacter calcoaceticus* | BNL-4-21 | 53996 |
| Arthrobacter sp. | BNL-4-22 | 53997 |

DETAILED DESCRIPTION OF THE INVENTION

The instant invention pertains to a new method of preparing microorganisms suitable for use in MEOR and to these modified microorganisms and their use in MEOR. More specifically, the instant invention relates to a method of modifying known microorganisms that exhibit characteristics that make them potentially attractive for MEOR, such as their ability to remains viable under high temperatures and pressures, through challenge growth processes, to obtain cultures useful in MEOR.

The present invention further relates to the development of thermophilic bacteria, especially those that are toxic metal resistant, modified using challenge growth processes, to make them useful for MEOR, which when used to treat crude oils at elevated temperatures and pressures comparable to those of reservoir conditions produce oils that: 1) are emulsified; 2) are acidified; 3) have a qualitative and quantitative change in light and heavy fractions of the crudes; 4) are chemically changed in the fractions containing sulfur compounds; 5) contain less trace metals such as nickel and vanadium, which appear to be solubilized; and 6) in which the quantitative and qualitative chemical and physical changes are dependent on the particular modified microbial species that is used. Microorganisms may be useful for MEOR if they adapt to the extreme reservoir environment.

The challenge growth processes are accomplished when microbial strains, selected because they have properties which may be useful in MEOR, are initially grown in a medium containing crude oil supplemented with other sources of nutrients, such as minerals and more easily metabolized sources of energy such as molasses and yeast extract. The strains which can survive in the presence of the crude oil are then subjected to further challenge by selection under more extreme conditions. The selection process proceeds by the removal of the more easily metabolizable carbon sources, i.e. the molasses, yeast extract and alike, while step wise increasing the temperature, pressure, salinity and varying the pH. Challenge growth processes are generally known in the art; see for example U.S. Pat. No. 4,780,238 to Premuzic which describes using this technique for the microbial production of chelating agents for detoxifying metal contaminants.

Table 1, which follows, lists many of the strains, produced through the challenge growth process, which modified microorganisms are useful in the oil recovery and oil treatment methods of the present invention. The modified microorganisms listed in Table 1 are illustrative of the many modified microorganisms that can be obtained following the challenge growth process that are useful for enhanced oil recovery or oil treatment. Table 1 lists the cultures that were subjected to the challenge growth process (see column "a") by the source of the original culture, ie. as deposited in the American Type Culture Collection ("ATCC #"), or the German Collection of Microorganism in Cell Cultures ("DSM #") (see column "b"). The modified microorganisms which result from the challenge growth process of the present invention are designated by Brookhaven National Laboratory number ("BNL #") (see column "c").

TABLE 1

| (a) Original Culture Designation | (b) Source/Depository | (c) Modified Microorganism |
|---|---|---|
| 1. *Acetogenium kivul* | DSM 2030 | BNL-6-10 |
| 2. *Acetomicrobium faecalis* | DSM 20678 | BNL-6-11 |
| 3. *Acetomicrobium flavidum* | DSM 20664 | BNL-6-12 |
| 4. *Achromobacter sp.* | ATCC 21910 | BNL-4-23 |
| 5. *Acinetobacter calcoaceticus* | DSM 3675 | BNL-6-13 |
| 6. *Anthrobacter sp.* | ATCC 21908 | BNL-4-22 |
| 7. *Azosoirillum halopraeferens* | DSM 3675 | BNL-6-13 |
| 8. *Bacillus caldolyticus* | DSM 405 | BNL-6-14 |
| 9. *Bacillus caldotenax* | DSM 406 | BNL-6-15 |
| 10. *Bacillus caldovelox* | DSM 411 | BNL-6-16 |
| 11. *Bacillus pallidus* | DSM 3670 | BNL-6-17 |
| 12. *Bacillus schlegelii* | DSM 2000 DSM 2001 | BNL-7-21 BNL-7-22 |
| 13. *Bacillus smithii* | DSM 459, 460, 2319, 2320, 2321 and 4216 | BNL-9-50 thru BNL-9-55 |
| 14. *Bacillus stearothermophilus* | ATCC 7953 | BNL-4-27 |
| 15. *Bacillus thermocatenultatus* | DSM 730 | BNL-6-18 |
| 16. *Bacillus thermoglucosidasius* | DSM 2542 DSM 2543 | BNL-7-23 BNL-7-24 |
| 17. *Bacillus tusciae* | DSM 2912 | BNL-6-19 |
| 18. *Calderobacterium hydrogenophilum* | DSM 2913 | BNL-6-20 |
| 19. *Chloroflexus aurantiacus* | DSM 635, 636, 637, 638 and ATCC 29363 | BNL-9-30 thru BNL-9-34 |
| 20. *Chromatium tepidum* | DSM 3771 | BNL-6-21 |
| 21. *Clostridium thermoaceticum* | DSM 521, 2955, ATCC 31490 and ATCC 39289 | BNL-9-10 thru BNL-9-13 |
| 22. *Clostridium thermoautotrophicum* | DSM 1974 | BNL-6-22 |
| 23. *Clostridium thermocellum* | DSM 1237, 1313, 2360, 4150 and ATCC 31924 | BNL-9-35 thru BNL-9-39 |
| 24. *Clostridium thermohydrosulfuricum* | DSM 567, 568, 569, 570, 2247, 2355 and ATCC 53016 | BNL-9-71 thru BNL-9-74, BNL-9-76, BNL-5-36, and BNL-5-37 |
| 25. *Clostridium thermolacticum* | DSM 2910 DSM 2911 | BNL-5-34 BNL-5-35 |
| 26. *Clostridium thermosaccharolyticum* | DSM 571, 572, 573, 869 and ATCC 31960 | BNL-9-40 thru BNL-9-44 |
| 27. *Clostridium thermosulfurogenes* | DSM 2229 DSM 3896 | BNL-7-27 BNL-7-28 |
| 28. *Desulfotomaculum nigrificans* | DSM 574, 575 and ATCC 7946 | BNL-8-10 thru BNL 8-12 |
| 29. *Desulfovibrio thermophilus* | DSM 1276 | BNL-6-23 |
| 30. *Dictyoglomus thermophilum* | DSM 3960 | BNL-6-24 |
| 31. *Leptospirillum sp.* | DSM 2391 DSM 2705 | BNL-5-30 BNL-5-31 |
| 32. *Microbispora bispora* | DSM 43038 ATCC 19993 | BNL-7-29 BNL-7-30 |

TABLE 1-continued

| (a) Original Culture Designation | (b) Source/Depository | (c) Modified Microorganism |
|---|---|---|
| 33. *Microbispora thermorosea* | DSM 43840 | BNL-6-25 |
| 34. *Nocardia paraffinae* | ATCC 21509 | BNL-4-25 |
| 35. *Pseudomonas sp.* | ATCC 21909 | BNL-4-24 |
| 36. *Pseudonocardia thermophila* | ATCC 19285 ATCC 21504 | BNL-6-25 |
| 37. *Rhodococcus sp.* | ATCC 21504 | BNL-4-26 |
| 38. *Sulfalobus sp.* | | |
| *acidocaldarius* | ATCC 33909 | BNL-TH-1 |
| *solfataricus* | ATCC 35091 | BNL-TH-29 |
| | ATCC 35092 | BNL-TH-31 |
| 39. *Thermoactinomyces candidus* | ATCC 27868 ATCC 29680 | BNL-7-33 BNL-7-34 |
| 40. *Thermoactinomvces sp.* | ATCC 14171, 14761, 14762 | BNL-8-13 thru BNL-8-15 |
| 41. *Thermoactinomyces vulgaris* | DSM 43016, 43050, 43062 DSM 43352 and ATCC 14570 | BNL-9-45 thru BNL-9-49 |
| 42. *Thermoactinomyces thalpophilus* | DSM 43353 | BNL-6-26 |
| 43. *Thermoactinomyces sacchari* | DSM 43356, ATCC 27349 and ATCC 27376 | BNL-8-16 thru BNL-8-18 |
| 44. *Thermoactinomyces intermedius* | DSM 43846 | BNL-6-27 |
| 45. *Thermoactinopolyspora coremialis* | ATCC 15974 | BNL-6-28 |
| 46. *Thermoactinopolyspora sp.* | ATCC 23550 ATCC 23551 | BNL-7-35 BNL-7-36 |
| 47. *Thermoanaerobacter ethanolicus* | DSM 2246, ATCC 31936, ATCC 31937, and ATCC 31938 | BNL-9-14 thru BNL-9-17 |
| 48. *Thermoanaerobacter finnii* | DSM 3389 | BNL-6-29 |
| 49. *Thermoanaerobium brochii* | DSM 1457 DSM 2599 | BNL-7-37 and BNL-7-38 |
| 50. *Thermobacteroides acetoethylicus* | DSM 2359 | BNL-6-30 |
| 51. *Thermodesulfobacterium commune* | DSM 2178 | BNL-6-31 |
| 52. *Thermomicrobium fosteri* | ATCC 29033 | BNL-6-32 |
| 53. *Thermomicrobium roseum* | ATCC 27502 | BNL-6-33 |
| 54. *Thermomonospora curvata* | ATCC 19995 | BNL-6-34 |
| 55. *Thermomonospora fusca* | ATCC 27730 | BNL-6-35 |
| 56. *Thermomonospora mesophilia* | ATCC 27303 | BNL-6-36 |
| 57. *Thermomonospora mesouviformis* | ATCC 27644 | BNL-6-37 |
| 58. *Thermoplasma acidophilum* | ATCC 25905, 27656, ATCC 27657 and 27658 | BNL-9-18 thru BNL-9-21 |
| 59. *Thermotoga maritima* | DSM 3109 | BNL-6-39 |
| 60. *Thermotoga neapolitana* | DSM 4359 | BNL-6-40 |
| 61. *Thermus aquaticus* | DSM 625, ATCC 25105, ATCC 27634 and ATCC 31558 | BNL-9-22 thru BNL-9-25 |
| 62. *Thermus flavus* | ATCC 33923 | BNL-6-41 |
| 63. *Thermus lacteus* | ATCC 31557 | BNL-6-42 |
| 64. *Thermus rubens* | ATCC 31556 | BNL-6-43 |
| 65. *Thermus sp.* | DSM 579 and DSM 674 ATCC 31674 | BNL-8-19 thru BNL-8-21 |
| 66. *Thermus ruber* | DSM 1279 | BNL-6-44 |
| 67. *Thiobacillus sp.* | | |
| *thiooxidans* | ATCC 15494, 19377, ATCC 8085, 21835 | BNL-3-23 to BNL-3-26 |
| *ferrooxidans* | ATCC 13598, | BNL-2-45 to |

TABLE 1-continued

| (a) Original Culture Designation | (b) Source/Depository | (c) Modified Microorganism |
|---|---|---|
| | 13661, 19859, 33020, 23270 and ATCC 21834 | BNL-2-49 |

Microbial mediated biochemical changes in crude oil can be caused by a single strain of microorganism or mixed cultures of microorganisms which are used subsequently under either aerobic or anaerobic conditions, depending on the ranges of salinity, pH, temperatures and pressures present in the geological formations.

For the purposes of the present invention, the preferred microorganisms are the thermophilic archaebacteria Sulfalobus sp., which have been modified by challenge growth processes. Most preferred are the modified microorganisms BNL-TH-1, BNL-TH-29, and BNL-TH-31, which were obtained from the parent strains *Sulfalobus acidocaldarius* (ATCC # 33909) and *Sulfalobus solfataricus* (ATCC # 35091 and 35092) modified through the challenge growth process. However, as shown in Table 1, many other varieties of thermophilic microorganisms have been modified to be suitable for MEOR and oil treatment, most of which particularly resemble acidophilic and halophilic bacteria. These modified bacterial strains are especially suitable for the present purposes because they remain viable under the harsh environmental conditions present in oil reservoirs with temperatures which may exceed 70° C.–85° C. and higher, and pressures which may exceed 2,000 p.s.i. up to about 2500 p.s.i.

When the modified microorganisms of the present invention are used in the biotreatment of crude oils, they are first grown to their maximum strength and maturity before they are added to the oil. Growing the modified microorganisms to their maximum before using them for biotreating the crude oil permits the biotreatment to take place at maximum efficiency, permits the microorganisms to continue to function for extended time periods at elevated temperatures and pressures, and results in the desired breakdown of the crude oil with removal of the sulfur compounds and metals.

Since trace metals such as nickel poison conventional "CAT" cracking catalysts which will be used subsequently to convert the crude to the final commercial products, the removal of metals through biotreatment, accomplished by the instant invention, yields a more commercially valuable crude. The metals are removed from the crude through the biotreatment at the same time the sulfur compounds are removed as both flow into the aqueous phase produced during biotreatment.

In conducting the experiments illustrating the present invention, as described in the following examples, small scale bioreactors illustrated in FIGS. 1 and 2 were constructed of stainless steel. These bioreactors were designed to incubate the microorganisms under increasingly higher temperatures and pressures. A glass, teflon or other inert material tube can be inserted for cultures of thermophilic bacteria that are sensitive to stainless steel.

Figure 2:
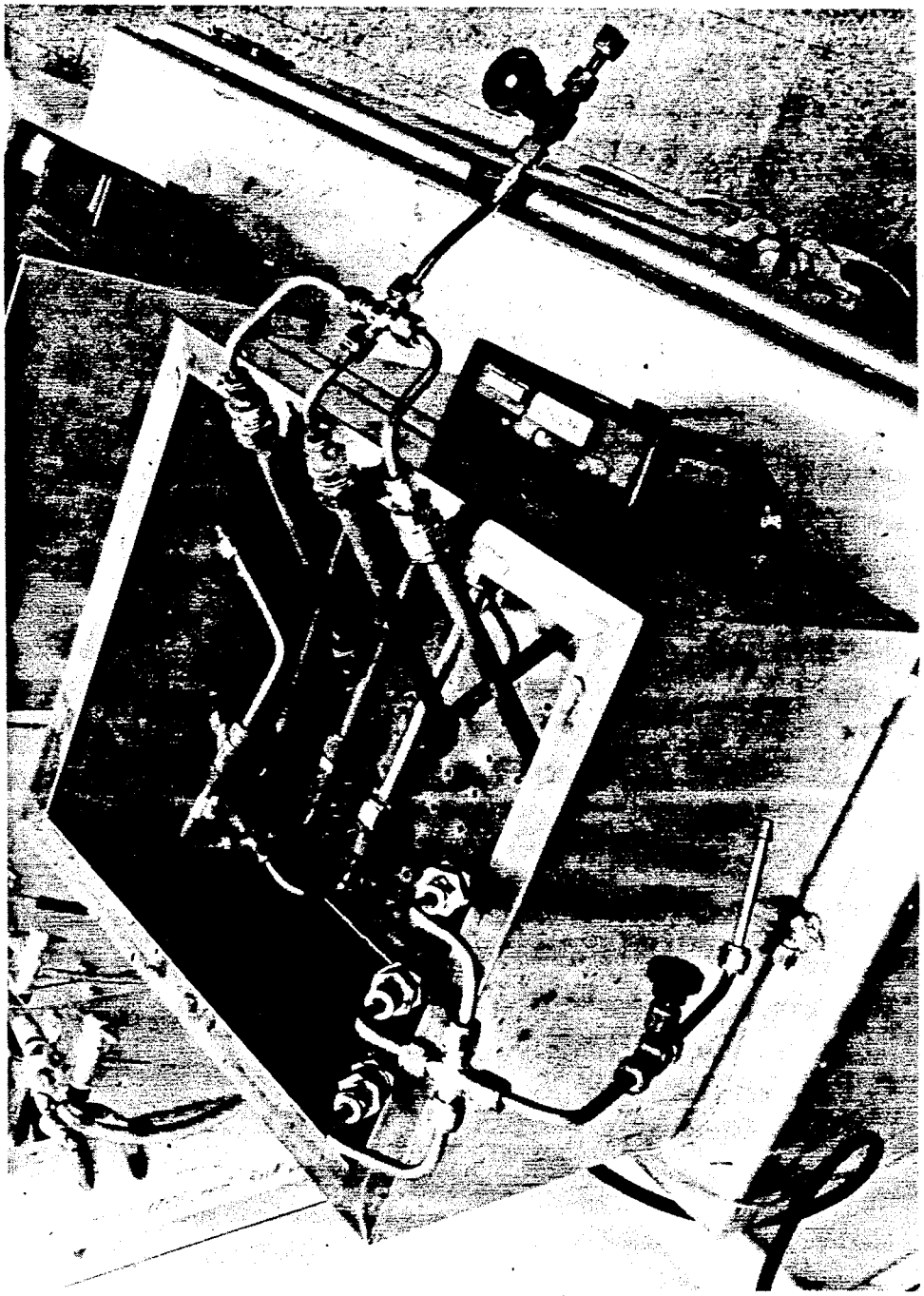
FIG. 2 is a photograph of the bioreactors in a temperature regulated water bath for preparing the microorganisms of the present invention.

The stainless steel bioreactors illustrated in FIGS. 1 and 2 can process from about 10–25 ml of culture medium. These bioreactors are able to withstand pressures of up to 8000 p.s.i. Design of the new bioreactor is based on the physical property of water between 4° C. to 100° C. In this temperature range, the density of water decreases as the temperature increases. If a water column is heated at the top, the hot and lighter water will stay at the top of the column while the cold and heavier water will remain at the bottom, and therefore, no convection will occur. In order to maintain the density as well as the temperature gradient, a metal tube, in this case aluminum, is used to enclose a long glass culture test tube. At the top end of the aluminum tube, an electric resistant heat unit is used as the heat source, while at the bottom end, cold water at 4° C. is used as a heat sink. In such a device, at steady state, a linear temperature gradient develops in the culture tube, which is maintained for long periods of time (weeks, months).

Over the experimental temperature range, remarkable small temperature fluctuations are observed. For example 4°–6° C. at the lower and 90°–95° C. at the upper range. After several days of incubation (4, 6, 10, etc.) microbial clusters appear at different temperature levels. These temperature zones for extended periods of time. The temperature zone adapted microorganisms can be transformed to fresh cultures at the "adaptation temperature", and maintained in stock cultures.

In the following experiments, the bioreactors were used for the challenge growth processes in a 70°–85° C. water bath (illustrated in FIG. 2) and pressures of 2000 to 2500 p.s.i., typically 2000 p.s.i. $N_2$ and 80 p.s.i. $CO_2$, at 70° C. Mini-bioreactors are used for anaerobic pressurized experiments while conventional culture flasks are used for aerobic experiments at elevated temperatures.

The culture medium for the challenge growth processes includes inorganic salts, e.g. $(NH_4)_2SO_4$, $MgSO_4$, $KH_2PO_4$ and crude oil or yeast abstract as a source of carbon. Incubations of cultures can be carried out under different pressures, gas compositions and temperatures. Yeasts, molasses and sources of carbon other than crude oil are used in conjunction with crude oil only at initial stages of growth. The organism is allowed to grow to a steady concentration, i.e. $1 \times 10^8$/ml under conditions in which the concentration of oil is increased and the other sources of carbon are decreased. During this initial stage, the organism is maintained at elevated temperatures and pressures. Generally, if the organism grows successfully to the desired level in the presence of crude oil as the sole source of carbon, but only at ambient temperatures, then it is "challenged" stepwise to higher temperatures and pressures until steady growth and desired concentrations are achieved. Two or three transfers at optimum conditions of growth often suffice to generate a modified microorganism suitable for MEOR.

The chemical composition of a crude oil makes it a complex matrix. Thus, in another aspect of the present invention, mixed cultures of microorganisms, preferably containing both aerobic and anaerobic organisms, are used to degrade and alter crude oils. Such organisms must be capable of growing at and/or adapting to elevated temperatures and pressures and must be able to grow in the presence of crude oils, salt brines and at pH extremes. By employing a mixed culture, it is possible to maximize the effect of the biotreatment by using a combination of organisms, each of which is very efficient in producing one or more of the desired degradation or adaptation of the crude oil. Following this approach, for example, a mixed culture could be used for biotreatment that contains one or more modified microorganisms that very efficiently affect emulsification, one or more modified microorganisms that produce organic acids, together with microorganisms that are generally effective for MEOR. The mixed culture approach permit tailoring of the microbial package used for biotreatment to the characteristics of the individual crude oil. It also permits taking advantage of the most effective characteristics of individual microorganisms modified for MEOR. The use of a mixed culture that contains aerobic and anaerobic organisms is particularly important if biotreatment is to be used in conjunction with water flooding to enhance the crude oil recovery.

Analysis of the crude oils that have been treated with the modified microorganisms of the present invention at temperatures of 65°–70° C. and pressures of 2000 psi $N_2$ and 80 psi $CO_2$ indicates that during the biotreatment, qualitative and quantitative changes in the composition of low and high molecular weight fractions has occurred. Further, the microorganisms used for the biotreatment were viable over extended periods of time (up to six months) and were able to tolerate extreme pH and high salt concentrations at 70° C. to 85° C. and 2000 to 2500 psi in the presence of crude oils as the sole source of carbon.

Accordingly, a collection of different microorganisms modified according to the present invention has been established which is being used in the biotreatment of crude oils over a wide range of experimental conditions. For instance, in the following Examples, treatment of Teapot Naval Petroleum Reserve No. 3 crude (PR3) oil with BNL-4-22 strain at 70° C. and 13.8 MPa resulted in acidification (a pH drop of 5 to 2) and emulsification of the reaction mixture during the biotreatment. Analysis of the aqueous phase indicated that lactic, propionic, isobutyric acids as well as butanol were produced during the biotreatment. Extent of emulsification of PR3 varied with different strains of microorganisms used. This was particularly evident when biosystems containing crude oils only as a sole source of carbon in the culture media were compared to those containing additional yeast as nutrients. Out of four treatments, biotreatment of PR3 as a sole source of carbon with one strain (BNL-4-22) resulted in an emulsified phase comparable or better to that in which a yeast extract has been added to the culture medium. Mass spectrometric analyses of treated and untreated PR3 showed major changes in the $C_6$–$C_{16}$ as well as the $C_{16}$–$C_{28}$ components, indicating biochemical alteration of higher molecular weight fractions. Extension of this experimental approach to a number of different oils, viz. Wilmington (California), Goch Saran (Iran), Recluse (Wyoming), Prudhoe Bay (Alaska), as well as heavy Venezuelan crudes, further supported the view, that in terms of MEOR the efficiency of biotreatment depends on the experimental conditions and the microbial species used as well as on the chemical composition of the particular crude oil. The biotreatment of the crude oils in the following examples under experimental conditions ranging from 30° C. to 80° C., ambient to 13.8 MPa pressures, and pH 1.5–7.5 revealed a number of unique and highly desirable properties of the temperature and pressure-adapted organisms of the present invention, and their potential for use in MEOR. These properties, which can be used to characterize and identify these new microorganisms, can be summarized as follows:

a. Compared to controls, biotreatment with the modified organisms produces overall changes in hydrocarbon content of heavy crudes. Qualitative analyses indicate that biodegradation of crudes occurs in heavy and lighter fractions of the oils.

b. Biotreatment produces changes in the composition of the organic sulfur components of the crudes, with a net overall effect being a decrease in the total sulfur content.

c. Biotreatment produces a decrease in the concentration of thianaphthalene organic compounds.

d. During the biotreatment, a number of organic acids are produced, ranging from small to larger molecular weight acids, which results in acidification of the crude mixture.

e. Studies of an emulsified phase have shown that hydrocarbons in the range of C13 to C26 are dispersed during the biotreatment.

f. Biotreatment produces a decrease in the C20 to C40 alkanes an increase in the <C20 type alkanes and an overall formation of lighter hydrocarbons.

g. Concurrent with changes in the organic composition of hydrocarbons, brought about by biotreatment, there are also changes in the composition of organometallic compounds.

h. The physicochemical changes brought about by biotreatment are organism specific and vary with different types of microorganisms.

i. Some microbial species biochemically prefer to convert higher molecular weight compounds to smaller, while others favor formation of better emulsions.

j. Trace metals are removed (most likely solubilized in aqueous phase) during biotreatment.

k. Pre-emulsification may lead to a significant enhancement in the overall biochemical effect.

l. Efficient emulsifying agents may be generated by some microorganisms and not others, with significant variable yields of desirable products.

m. Biochemical modification and/or removal or organic sulfur compounds with a concurrent removal of trace metals from Cerro Negro and Boscan crudes by microorganisms of the present invention indicates that biotreatment of high sulfur content crude oils may lead to a desulfurization process for these types of oils.

Additionally, the following examples show that there is a considerable complexity in the processes by which microorganisms interact with crude oils. However, certain trends are beginning to emerge as seen in molecular weight distribution, sulphur content, emulsification and changes in trace metal contents. Different effects are also observed when different oils are treated by the same microorganisms. For example, Boscan crude oil is heavy due to immaturity and Cerro Negro is heavy due to biodegradation. It is clear that the microbial action on the biodegradable Cerro Negro is different than that on the Boscan, not only because of their chemical differences, but also because the "naturally" biodegraded oil must change during the biotreatment by the microbial organism of the present invention in a manner different to that occurring during biodegradation in a reservoir over geological periods of time.

The following Examples have been carried out to show that the effects of different microorganisms on crude oils depend on microbial species and types of oils used. The changes brought about by biotreatment result in different emulsions, and removal of organic sulfur and trace metals. There are also qualitative and quantitative changes in the distribution of high and low molecular weight fractions, all with noticeable species dependence. Accordingly, in order to explore and document these observations, measurements of various properties of biotreated oils have been carried out in the following examples which study the bioprocess(es) and characteristics of biotreated oils.

These examples further illustrate the various features of the invention, and are not intended in any way to limit the scope of the invention which is defined in the appended claims.

EXAMPLES

Materials and Methods

1. Bioreactors

Small-scale bioreactors as shown in FIGS. 1 and 2 are employed with or without glass, teflon or other inert material inserts. Each bioreactor can handle a total volume of 20 ml of fluid and can be re-used many times. Typically in each experiment, three bioreactors were used. Thus, one bioreactor was charged with nutrients in water, gases ($CO_2$, $N_2$) and the experimental organism only. A second bioreactor was charged with oil, gases ($CO_2$, $N_2$), and nutrients in water. A third bioreactor was charged with oil, microorganisms, gases ($CO_2$, $N_2$), nutrients, and water. All were kept under identical experimental conditions of temperature and pressure.

2. Instrumentation a) Gas chromatography—Mass spectrometry (GC/MS)

A Perkin-Elmer (PE) model 8700 microprocessor-controlled gas chromatograph (GC) with multiramp temperature programming, has been used in all GC work. The PE 8700 was interphased with a PE-Finnigan Ion Trap Detector (ITD) for mass measurements in the 20-650 mass units range. This gas chromatography-mass spectrometry system (GC-MS) encompasses the NBS/EPA mass spectral library. The PE 8700 GC system is also equipped with a Flame Ionization Detector (FID) and Flame Photometric Detector (FPD).

b) High pressure liquid chromatography (HPLC)

High pressure liquid chromatography was carried out on a Spectra Physics SP 8750 manufactured by Spectra Physics, Inc., San Jose, Calif..; and on an Aminex HPX-87H exclusion column from Biorad Laboratory, Cambridge, Mass.

c) Metal Complexes

Hewlett-Packard gas chromatograph model HP5921A equipped with atomic emission detector was used for the determination of metal complexes. For multi-elemental analyses, Induced Coupled Plasma Mass Spectrometry (ICP-MS) was conducted on a UG-Fisons Instrument Plasma Quad II Plus, VG Instruments, Danvers, Mass.

d) Sulfur Analysis

Total sulfur was determined by combustion (Huffman Laboratories, Golden, Colo.). The organic sulfur compounds were monitored by GC from 40°-300° C. equipped with a Flame Photometric Detector (FPD). A J&W, DBI column was used throughout. Characterization of changes in groups of sulfur compounds present in oil, e.g., sulfides, thiophenes and sulfoxides has been carried out by means of XANES analysis (Huffman, et al., *Energy & Fuels*, 1991, 574–581).

e) Emulsification

The extent of emulsification produced by different microorganisms was determined by literature methods [Rosenberg, et al., *Appl. and Environ. Microbial.*, 37(3), 402-408 (1979)] and expressed in Klett units given by $$\frac{1000 \times D}{2},$$

where D is the absorbance determined at 545 nm. Viscosity of emulsions produced by different microorganisms was determined with an LVT viscometer (Brookfield, Model LVT viscometer) at 25° C. and expressed in Centipoises.

f) pH Measurements

The extent of acidification (pH measurements) was measured with an Orion Research, Inc. pH meter (Model 901) according to the manufacturer's instructions.

3. Growth and Adaptation of Microorganisms

Culture media consisted of inorganic salts, e.g., $(NH_4)_2SO_4$, $MgSO_4$, $KH_2PO_4$, and crude oil or yeast extract as a source of carbon. Incubations were carried out at different temperatures (from 4° C. to >85° C.) and pressures (200-2500 psi). Through challenge growth processes, which makes it possible to adapt microorganisms to different pressures and temperatures, several different species and strains of microorganisms have been developed. Those used in the examples that follow are listed with the summary of the appropriate treatment in Table 2.

Bacterial growth was analyzed by counting and turbidity measurements at 600 and 660 nm on a Beckman Acta III grating spectrometer from Beckman Instruments.

In challenge growth processes, a parent strain was allowed to grow to its maximum growth ($\geq 10^8$ organisms per ml.) in a mixture of known volume of crude oil viz., one ml, and known volume of culture medium viz. 10 ml. (e.g. yeast extract, amino acids, $KH_2PO_4$, $(NH_4)_2SO_4$, $MgSO_4.7H_2O$, $CaCl_2$; $2H_2O$, $MnCl_2.4H_2O$, $Na_2B_4O_7.10H_2O$, $ZnSO_4.7H_2O$, $CuCl_2.2H_2O$, $Na_2MoO_4.2H_2O$, $VOSO_4.2H_2O$, $CoSO_4.7H_2O$, distilled water), pH adjusted to 4.0 initially and then sterilized. The mixture was allowed to grow at 70° C. under pressure (2000 psi of $N_2$ and 80 psi $CO_2$). The two phase system was incubated for five to seven days without shaking. The microbial growth at this step usually exceeded a concentration of $5 \times 10^7$/ml. The active biomass was then transferred to an identical system as initial, except that the organic source (e.g. yeast extract, amino acids) were reduced by 90%. The incubation was then allowed to proceed as normal. The number of transfers and incubations as described above varies with different strains and is usually repeated several times (2, 3 or more). This procedure yields a modified strain capable of efficient growth in the presence of crude oil and about 4% $CO_2$ as the sole sources of carbon under the experimental conditions described. This procedure was used to prepare all the modified organisms described in Table 1 and 2 and the following examples.

TABLE 2

| Modified Microorganism | Treatment Conditions | | | |
|---|---|---|---|---|
| | Temp. °C. range | Medium | Pressure psi | pH |
| BNL-TH-29 Sulfalobus | 60–80 | A | up to 2000 | 1.5–4.5 |
| BNL-TH-31 Sulfalobus | 60–80 | A | up to 2000 | 1.5–4.5 |
| BNL-4-21 Acinetobacter | 25–75 | B | Atm. | 6–7.5 |
| BNL-4-22 Arthrobacter | 25–75 | B | Atm. | 6–7.5 |
| BNL-4-23 Achromobacter | 25–75 | B | Atm. | 6–7.5 |
| BNL-4-24 Pseudomonas | 25–75 | B | Atm. | 6–7.5 |
| BNL-4-25 Nocardia | 0 | C | Atm. | 7 |
| BNL-5-32 Methanogenium | 55–60 | D | Atm. | 6–7.5 |
| BNL-TH-1 Sulfalobus | 60–80 | E | up to 2000 | 1.5–2.5 |
| BNL-3-25 Thiobacillus | 30–60 | F | 100 | 1.0–2.5 |
| BNL-4-32 Acidophilic thermophile | 30–60 | G | 100 | 1.0–2.5 |

Medium A is ATCC designated medium 1304, supplemented with a non-peptone modified carbon source. Medium B is a nutrient broth containing beef extract supplemented by a non-peptone carbon source. Medium C is a yeast extract medium. Media D and E are ATCC designated media 1442 and 1256, respectively, also supplemented with non-peptone modified carbon source. Medium F is a basal salt solution, and Medium G is a basal salt solution supplemented with iron su lfate. In each case, crude oil becomes the sole carbon source in the final adaptation at the upper temperature limit.

4. Crude Oils

Seven (7) crude oils were utilized in these experiments, Recluse, Teapot Naval Petroleum Reserve #3 (designated "PR3"), Goch Saran (Iran), Wilmington crude, two Venezuelan crudes-Boscan and Cerro Negro, and Prudhoe Bay an Alaskan crude oil, all provided by the U.S. Department of Energy, Bartlesville Project Office. Recluse is a cretaceous crude oil from Recluse, Wyoming as described by Thompson et al., "Analyzing Heavy Ends of Crude", *Hydrocarbon Processing*, 93–98, (1974). PR3 is a crude oil from the Salt Creek Anticline Area, Powder Basin, Wyo., as described by Tillman et al. in "The Shannon Shelf-Ridge Sandstone Complex, Salt Creek Anticline Area Powder Basin, Wyo.", *Silicastic Shelf Sediments*, Tilman et al. (eds.), Soc. of Economic Paleontologists and Mineralogists, 34, 85–142 (1984). The Wilmington crude was obtained from the U.S. Department of Energy, Bartlesville Project Office and is described in the Thompson, et al. paper cited above.

Example 1

The modified *Sulfalobus acidocaldarius* strain designated BNL-TH-1 was used to biotreat each of the three crude oils, Recluse, PR3 and Wilmington Crude.

For each type of oil, three bioreactors were utilized under identical experimental conditions. One bioreactor contained nutrients in water, gases ($N_2$, $CO_2$) and the experimental organism BNL-TH-1. The second bioreactor contained oil (1.0 ml), gases ($CO_2$, $N_2$), inorganic salts and yeast extract only. The third bioreactor contained oil (1.0 ml), the microorganism BNL-TH-1, inorganic salts, no yeast extract, and gases ($CO_2$, $N_2$). The incubation was carried out at 70° C. with the partial pressures for $CO_2$ and $N_2$ being 80 psi and 2000 psi respectively. Each was maintained for three weeks in the water bath shown in FIG. 2. After a steady count of microorganisms was achieved, e.g., $1 \times 10^8$, the organisms were transferred into freshly charged bioreactors as described in the Materials and Methods section above and the microbial growth was allowed to continue another three weeks.

FIG. 3 shows the GC-MS analysis of untreated Recluse crude comparing (a) untreated oil verses (b) oil which had been treated with the modified *Sulfalobus acidocaldarius* species (BNL-TH-1), as described above. The changes in the heavy ends of the biotreated crude are especially pronounced. There is an apparent decrease in the high molecular weight components. A GS-MS scan for mass M/e 32 signal representative of sulfur compounds is shown in FIG. 4 for the (a) untreated and (b) treated crude oil. The scan shows significant change in the biotreated oils.

Changes in the Hydrocarbon Composition of Crudes

Example 2

The possibility that various emulsification effects may also reflect chemical changes brought about by the biotreatment of crudes was explored by treatment of PR3 with modified organisms BNL-4-2 and BNL-4-22. The changes in the composition of hydrocarbons in the organic phase were followed by gas chromatography/mass spectrometry (GC/MS).

Figure 9A:
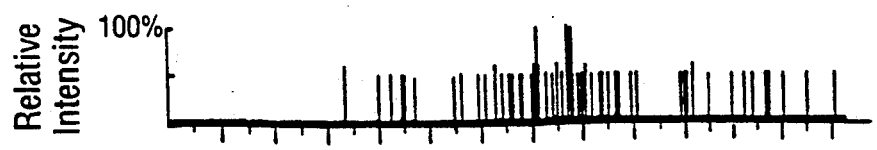
FIG. 9 shows degradation of cyclic hydrocarbons, (a) before treatment and (b) after treatment, m/e 123 ion trace of PR3 crude treated with BNL-4-24.
Figure 9B:
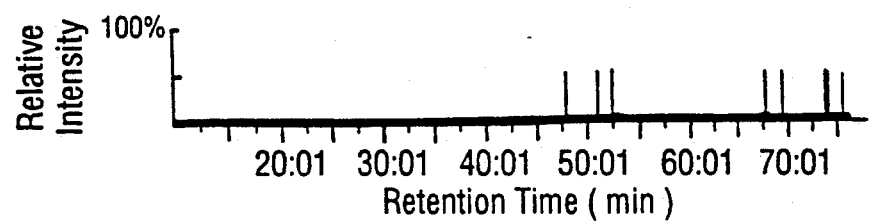

The organisms were cultured for a period of two to four weeks in the presence of 10–18% by volume of crude oil with no other carbon source in the media. Analysis by GC/MS shows that there are significant alterations in the distribution of hydrocarbons, particularly in the regions of lower and higher molecular weight compounds. The microbial effects on the hydrocarbon composition changed between the different strains used. In order to further explore the biochemical action of microorganisms on crude oils, GC/MS system was used to analyze for diagnostic molecular markers. In the mass spectromatic analysis of mixtures containing organic compounds, such as crude oils, it is customary to use characteristic masses generated during fragmentation of organic molecules. For example, $C_4H_9$ (m/e 57) for alkanes, $C_7H_7$ (m/e 91) for substituted aromatics and others, etc., all of which are characteristic molecular markers [Williams et al., *Petroleum Geochemistry*, Pergamon Journals Ltd., pp. 451–461 (1986)]. Biotreatment of PR3 with microbial strain BNL-4-24 at 65° under 2000 psi of nitrogen and 80 psi of carbon dioxide for two weeks yielded the following results: The single ion chromatogram monitored for mass 57 (FIG. 5), shows that the lighter alkanes (up to C16) were degraded over that period of time, while those hydrocarbons which were larger than C16 and up to C30, based on peak comparison, were about 80% degraded. Similarly, FIG. 6 shows the effect of the biotreatment on alkylaranes (m/e 91), FIG. 7 on C-3 naphthalenes (m/e 169), and FIG. 8 on cyclic hydrocarbons, e.g., adamantine type (m/e 135). Considerable biodegradation of other cyclic saturated hydrocarbons, e.g., bicyclic sesquiterpanes (m/e 123) also occurs, as shown in FIG. 9.

Figure 10A:
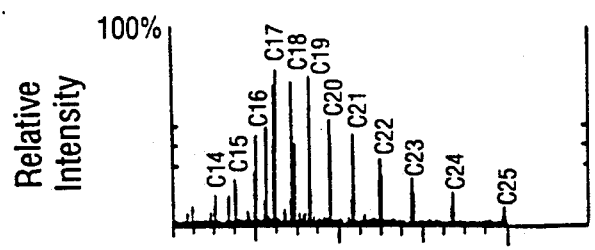
FIG. 10 shows changes in the alkane composition of PR3 crude: (a) Control; (b) PR3 treated with BNL-4-25; and (c) PR3 treated with BNL-5-32.
Figure 10B:
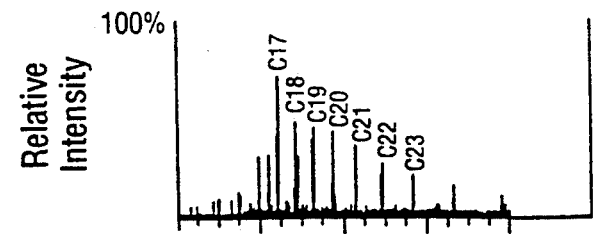
Figure 10C:
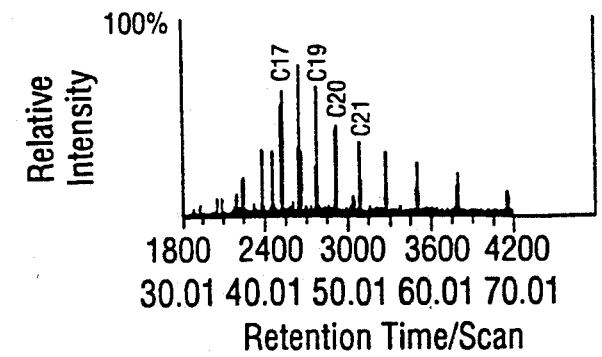
Figure 11A:
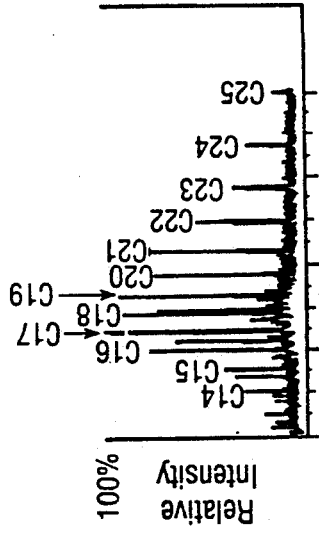
FIG. 11 shows changes in the alkaline composition of PR3 crude: (a) Control; (b) PR3 treated with BNL-4-25; and (c) PR3 treated with BNL-5-32.
Figure 11B:
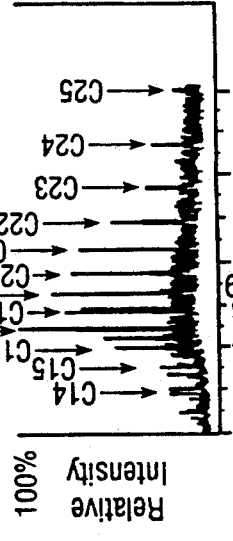
Figure 11C:
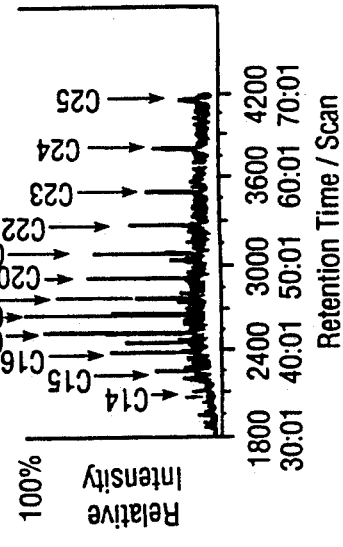
Figure 12A:
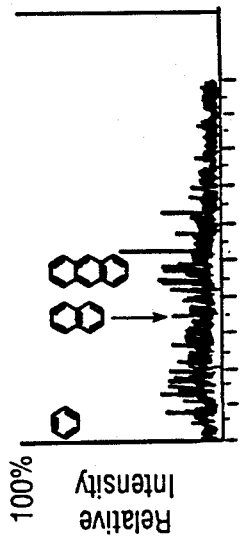
FIG. 12 shows changes in the aromatics composition of PR3 crude: (a) Control; (b) PR3 treated with BNL-4-25; and (c) PR3 treated with BNL-5-32.
Figure 12B:
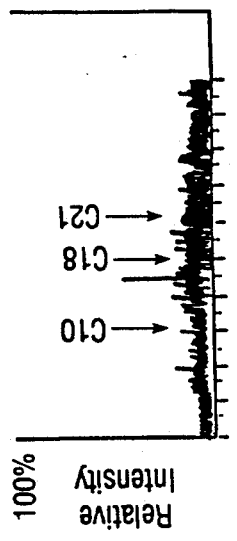
Figure 12C:
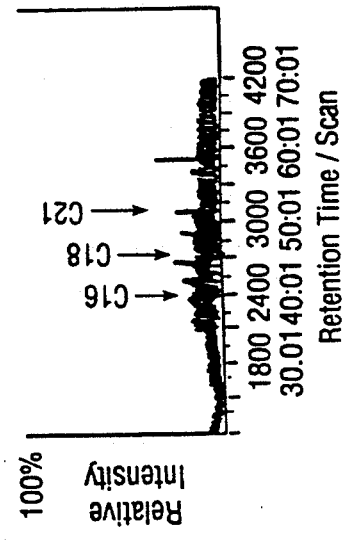

The results shown in FIGS. 5–9 show that the treatment of PR3 with a thermophilic pseudomonas, BNL-4-24, affects characteristically both lighter (C16) and heavier (up to C30) alkanes, aromatics, and sesquiterpane types of compounds. Similar studies were conducted with other modified microbial species under the same temperature and pressure conditions. Thus, treatment of PR3 with BNL-4-25 and BNL-4-3 resulted in qualitative and quantitative changes of alkanes, alkenes, and aromatics as shown in FIGS. 10-12.

These results clearly show that there exist considerable differences between the action of BNL-4-24, BNL-4-25, and BNL-4-32 on PR3. For example, the m/e 57 scan for BNL-4-24 treated crude suggests a larger effect on the oil than that brought about by BNL-4-25 and BNL-4-32 in the same molecular range of hydrocarbons. Although the chemical interactions between the microorganisms and oils are complex, the use of molecular markers makes it possible to observe and follow chemically characteristic patterns associated with these interactions. Further the use of ion-scans and other diagnostic parameters will lead the development of a data base which should ultimately determine trends and variations in the composition of biotreated crude oils.

Example 3

Figure 14:
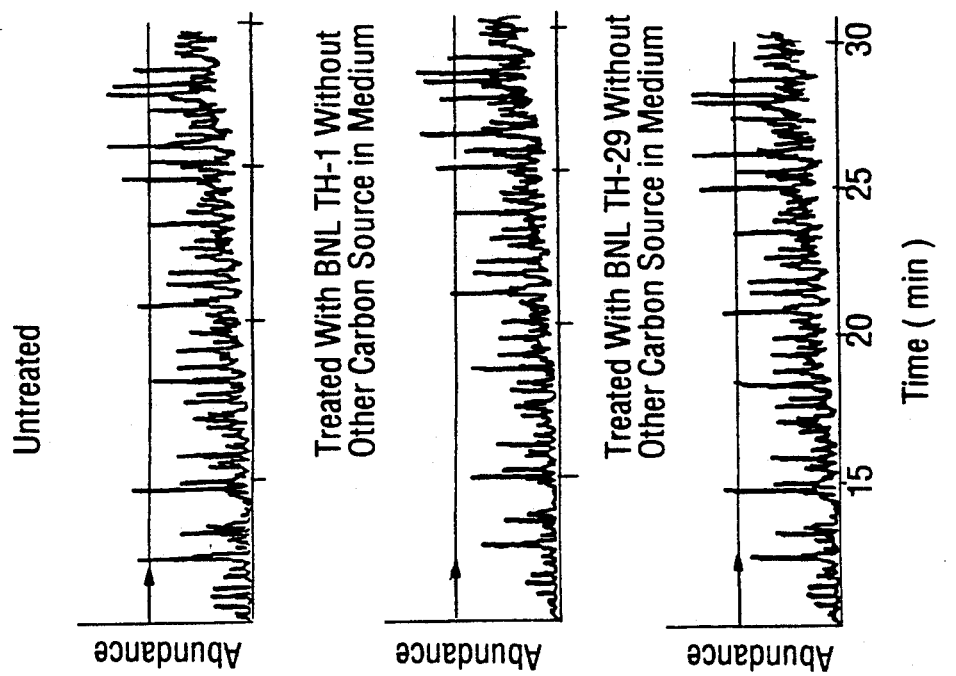
FIG. 14 is a GC-MS Total Ion Chromatogram 30 Min. scan of PR3 crude oil (a) untreated, (b) biotreated with (BNL-TH-1) without other carbon source in the medium, and (c) biotreated with (BNL-TH-29) without other carbon source in the medium.
Figure 13:
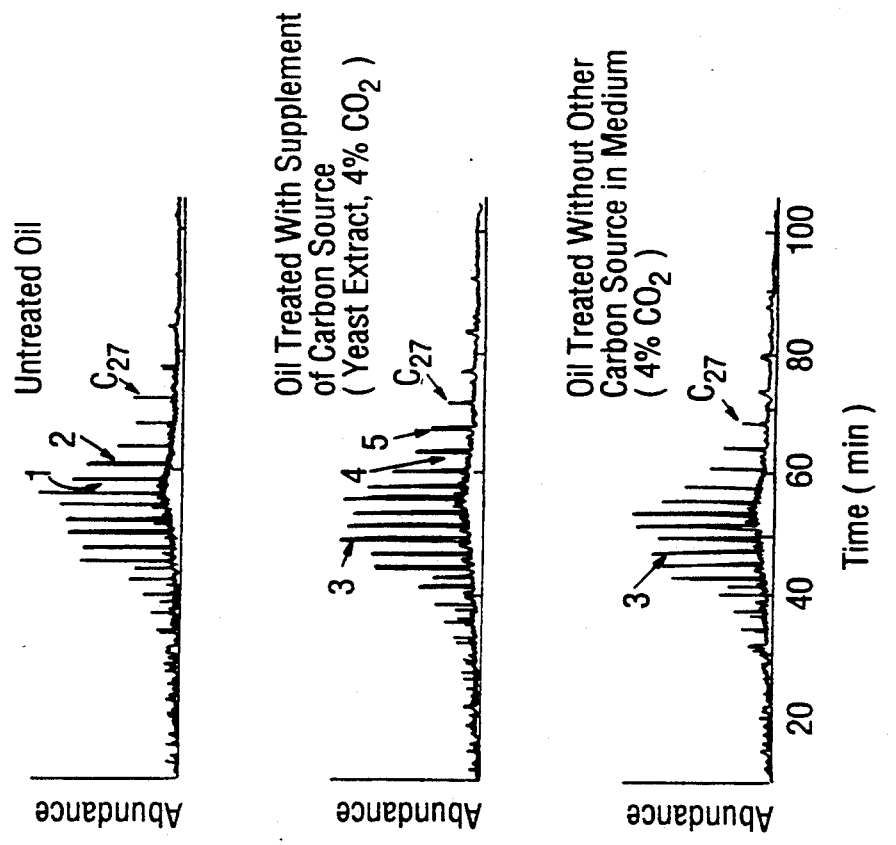
FIG. 13 is a GC-MS Total Ion Chromatogram 100 Min. scan of PR3 Crude Oil (a) untreated (b) biotreated with BNL-TH-1 supplemented with carbon source (yeast extract) in medium (4% $CO_2$); and (c) biotreated with BNL-TH-1 without other carbon source in medium, (4% $CO_2$).
Figure 16:
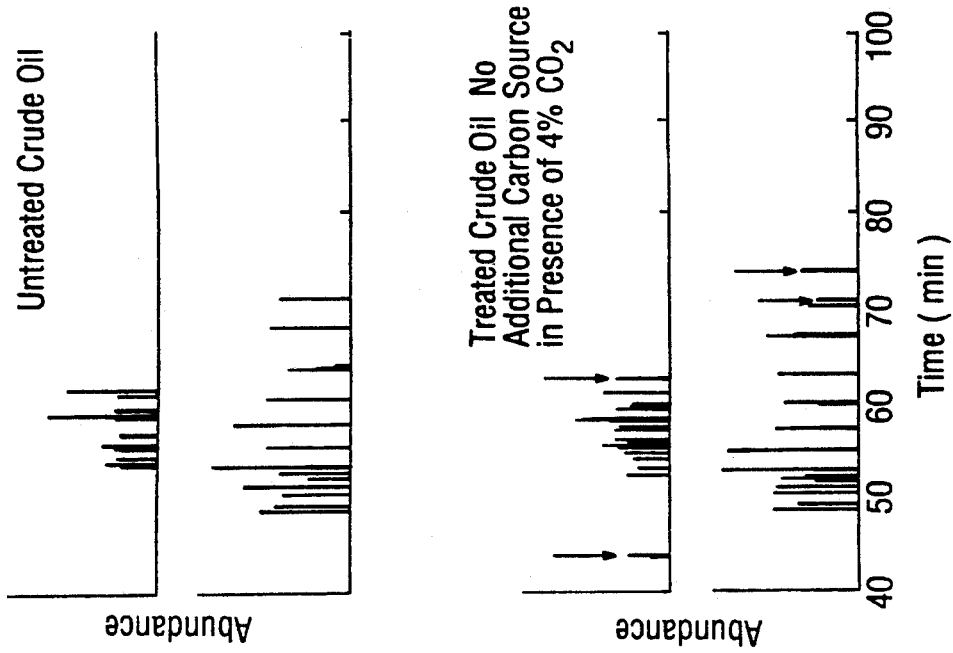
FIG. 16 shows the mass signal 231 [for triaromatized steroids] and a mass signal 253 [for monoaromatized steroids] mass fragmentation scans for (a) untreated PR3, and (b) PR3 biotreated with (BNL-TH-1) with no additional carbon source in the presence of 4% $CO_2$ at 70° C. and 2000 p.s.i.
Figure 15:
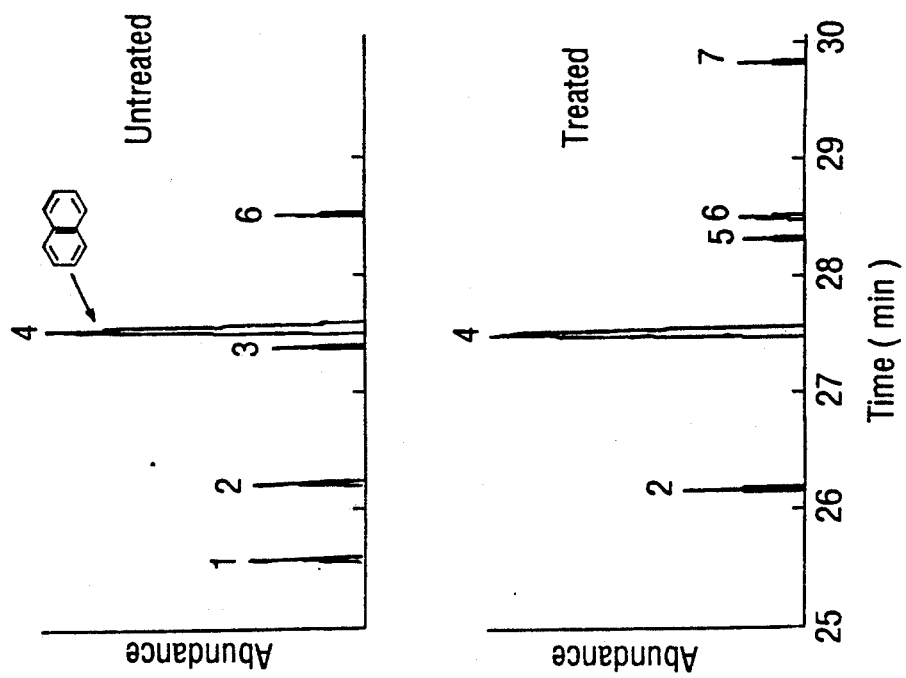
FIG. 15 shows the M/Z 127, Mass Fragmentation pattern showing the naphthalenes region of PR3 (a) untreated, and (b) biotreated with (BNL-TH-1).

A 100 minute GC-MS Total Ion Chromatogram scan of PR3 biotreated at 70° C. and 2000 psi with modified *Sulfalobus acedocaldarius* species (BNL-TH-1) is shown in FIG. 13. There is a notable difference in the area of peaks 1 and 2 and the appearance of new peaks 4 and 5. FIG. 14 shows the expansion of the 30 minute scan of (a) untreated PR3 (b) PR3 treated with modified *Sulfalobus acidocaldarius* species (BNL-TH-1), and (c) PR3 biotreated with modified *Sulfalobus solfactaricus* species (BNL-TH-29), respectively, each without any other carbon source in the medium, showing changes in the overall concentration of alkanes and monoaromatics. The M/Z 127 mass fragmentation pattern indicative of the naphthalenes region is illustrated in FIG. 15 where BNL-TH-1 was used. After treatment, with the modified microorganism BNL-TH-1, peaks 1 and 3 were removed, and peaks 5 and 7 appeared as a consequence of the breakdown of a higher molecular weight fraction. FIG. 16 shows the M/Z 231 and M/Z 253 scan characteristic of the tri- and mono-aromatized styrene fragmentation pattern, which also indicates the appearance of new peaks (see arrows). These new peaks are probably due to a breakdown of higher fractions such as tars caused by the action of BNL-TH-1.

These results suggest some similarities between controlled biodegradation of crude oil over a short period of time (in days) and natural biodegradation of crude oil over a long period of time (in millions of years) as reported by Williams, et al., "Biodegradation in South Texas Eocene Oils-Effects On Aromatics and Biomarkers.", *Organic Geochem.*, 10, 451–461 (1986).

Acidification of crude oils

Example 4

Figure 17:
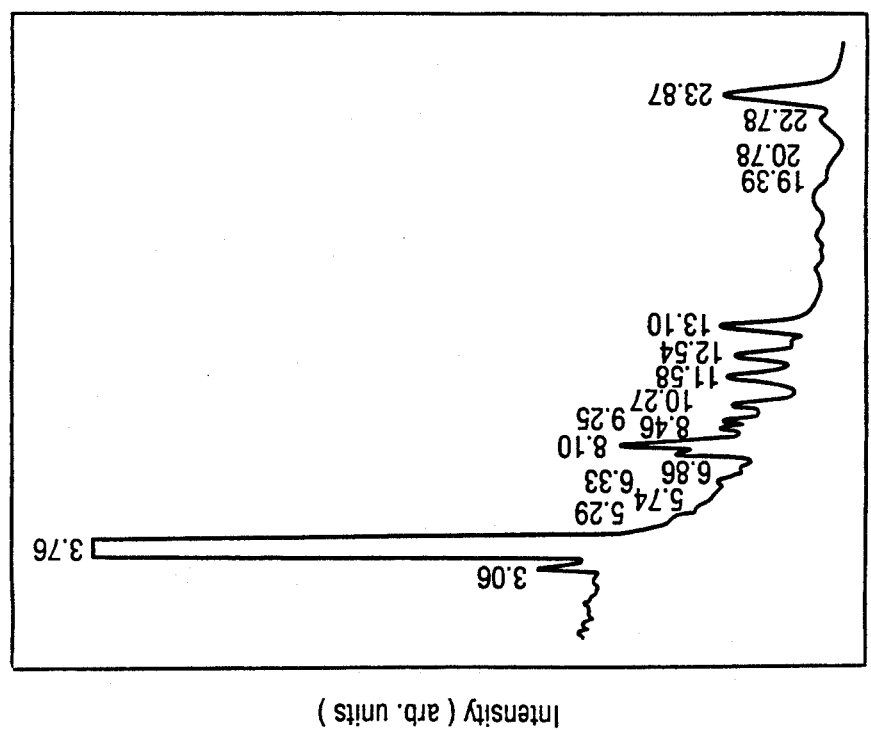
FIG. 17 shows High Pressure Liquid Chromatography (HPLC) analyses of metabolites produced by biotreatment of PR3 with BNL-4-22., These metabolites are emulsifying agents produced from the oil.

Earlier experimental observations have shown that there are significant changes in the pH of the medium during the microbial action on crude oil under the experimental conditions described in Example 1. These changes were determined by direct measurement of pH. The observed drop in pH was from 5 to 3 indicating that the aqueous phase should be analyzed for water soluble acidic compounds produced by microbial treatment as the possible causes of acidification. Accordingly, high pressure liquid chromatographic (HPLC) analysis was carried out on a sample of PR3 crude which was treated with the modified Arthrobacter sp. strain (BNL-4-22) of the present invention. The result is shown in FIG. 17. Analysis of the results shows that there are a number of components present which include lactic, propionic, isobutyric acids and n-butanol, respectively. While these acids by themselves may be responsible for the acidification and emulsification of the reaction mixture, other, less than usual metabolic products such as sulfonic acids, aromatic carboxylic acids, which were not analyzed for in this experiment, may also contribute to the acidification.

Emulsification of Crude Oils by Biotreatment

Example 5

Figure 18:
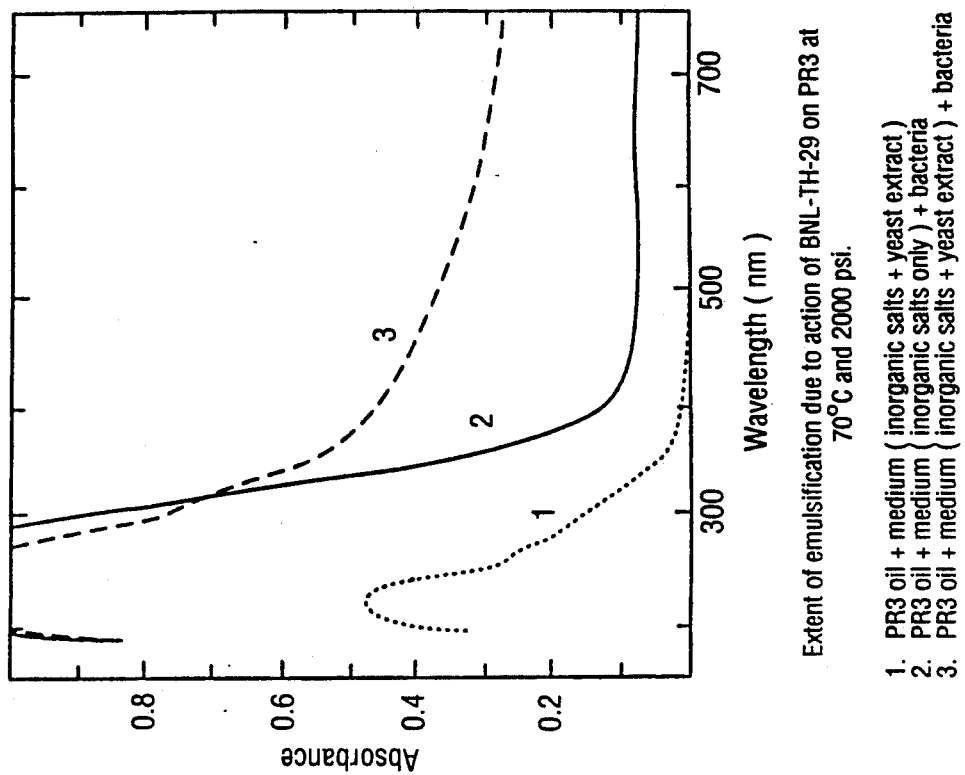
FIG. 18 shows the extent of emulsification due to biotreatment of PR3 with (BNL-TH-29) at 70° C. and 2000 p.s.i. on (1) PR3 oil+medium (inorganic salts+yeast extract); (2) PR3 oil+medium (inorganic salts only)+bacteria; (3) PR3 oil+medium (inorganic salts+yeast extract)+bacteria.

Biotreatment of PR3 with the modified microorganisms of the present invention produces emulsification of the reaction mixture. The spectrophotometric analysis of modified *Sulfalobus solfataricus* species (BNL-TH-29) treated PR3 crude oil is shown in FIG. 18. This experiment shows that a considerable biochemical reaction occurs when crude oil is the only carbon source in the media (spectrum #2). The extent of emulsification of PR3 by BNL-4-24 (1); BNL-4-23 (2); BNL-4-22 (3); and BNL-4-21 (4) is shown in FIG. 19.

Figure 19:
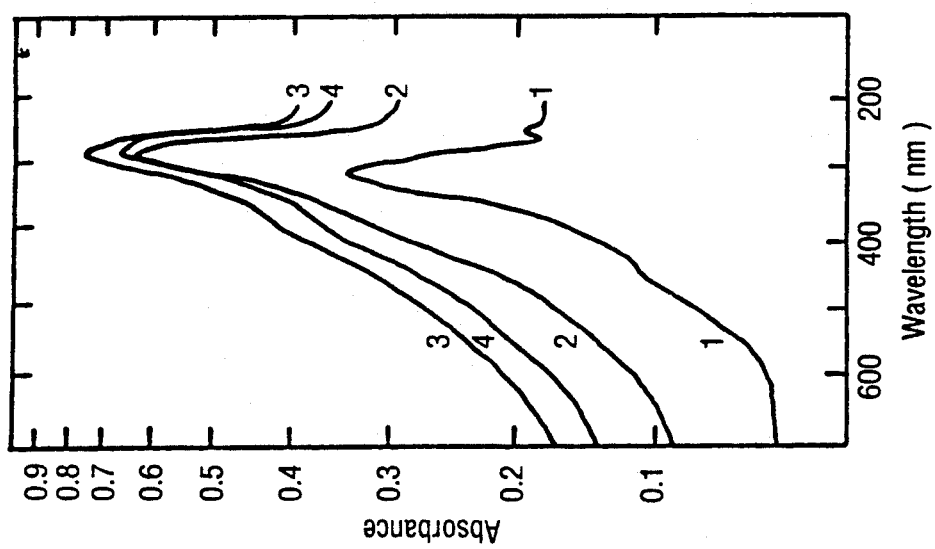
FIG. 19 shows the extent of emulsification (700–200 nm spectral region) of PR3 by (1) BNL-4-24; (2) BNL-4-23; (3) BNL-4-22; and (4) BNL-4-21.

As shown in FIGS. 18 and 19 and Table 3 below, treatment of PR3 with several strains of thermophilic microorganisms resulted in different emulsifying effects, suggesting that certain microbial species may produce more efficient surfactants than others. Further, it may also be possible that interactions between microorganisms and crude oils could exhibit microorganism/crude oil species specificity and/or selectivity.

TABLE 3

Extent of emulsification due to the action of various microorganisms on heavy fractions of crude oils. The results are expressed in Klett units

| Micro-organisms | Wilmington[1] (Calif) | Goch Saran[1] (Iran) | Heavy Oil Fraction | |
| --- | --- | --- | --- | --- |
| | | | Recluse[1] (Wyo) | Prudhoe[1] (Alaska) |
| BNL-4-24 | 115 | 168 | 250 | 215 |
| BNL-4-23 | 290 | 238 | 225 | 195 |
| BNL-4-22 | 252 | 320 | 175 | 285 |
| BNL-4-21 | 515 | 142 | 600 | 615 |

[1]Heavy fractions (200° C.) of crude distillate

Example 6

In order to determine the effects of various microorganisms, modified according to the present invention, on PR3 (and other crudes) under the experimental conditions of the present invention. Therefore, a series of experiments were initiated in which different modified strains of microorganisms, generated as described above, were allowed to act on the same oil under identical experimental conditions as described in Example 1. The purpose of these studies was to develop a data base of efficient "emulsifiers" and "acidifiers" and relate this to experimental conditions and chemical changes.

Figure 20:
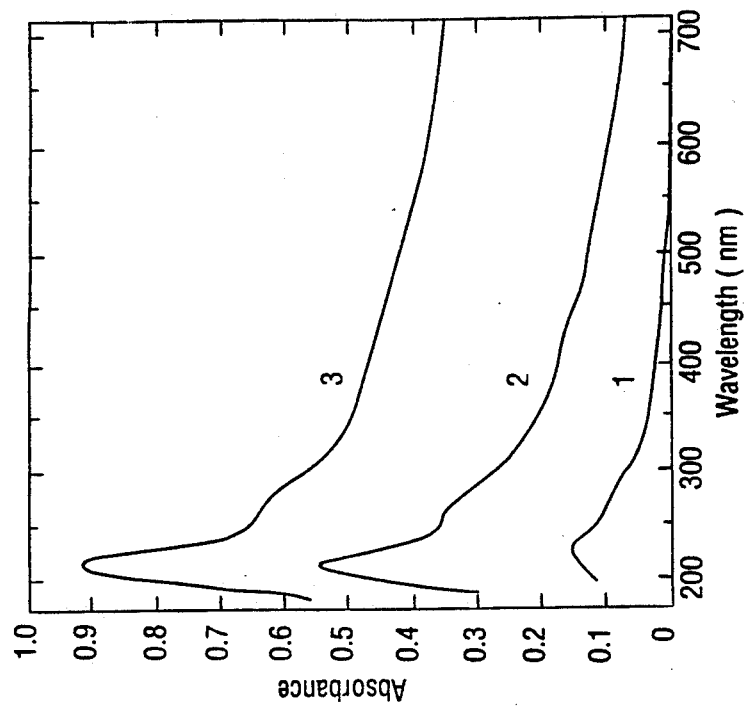
FIG. 20 shows the extent of emulsification due to biotreatment of modified *acinobacter calcoaceticus* (BNL-4-21), and modified *Anthrobacter sp.* (BNL-4-22) at 70° C. and 2000 p.s.i.; (1) PR3 oil+medium; (2) PR3+BNL-4-21; and (3) PR3+BNL-4-22.
Figure 21A:
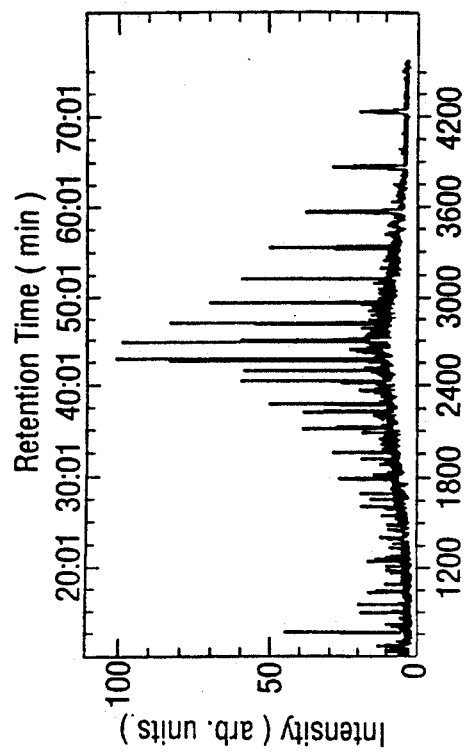
FIG. 21 is a gas chromatographic analysis of PR3 (a) untreated; and (b)/ biotreated at 70° C. and 2000 p.s.i. with modified *Acinetobacter calcoaceticus* (BNL-4-21).
Figure 21B:
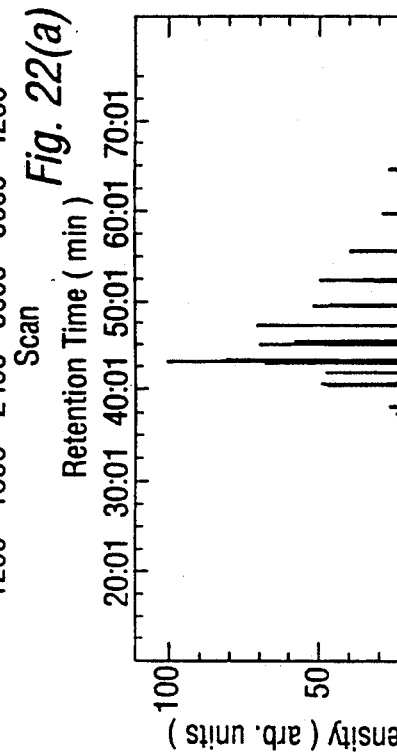
Figure 22A:
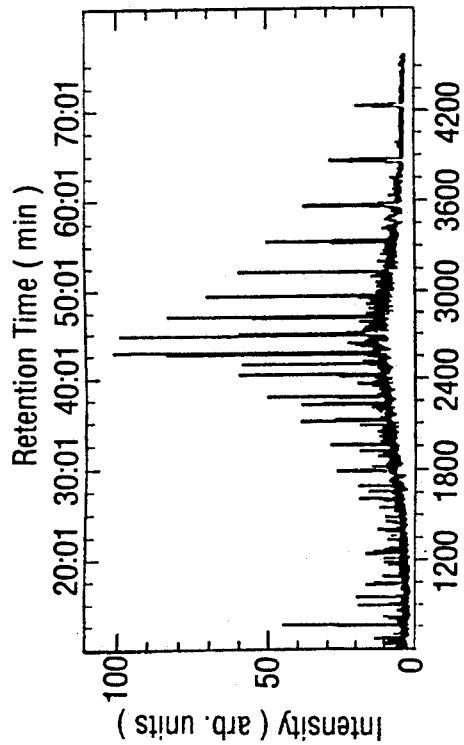
FIG. 22 is a gas chromatographic analysis of PR3 (a) untreated; and (b) biotreated with *Anthrobacter sp.* (BNL-4-22).
Figure 22B:
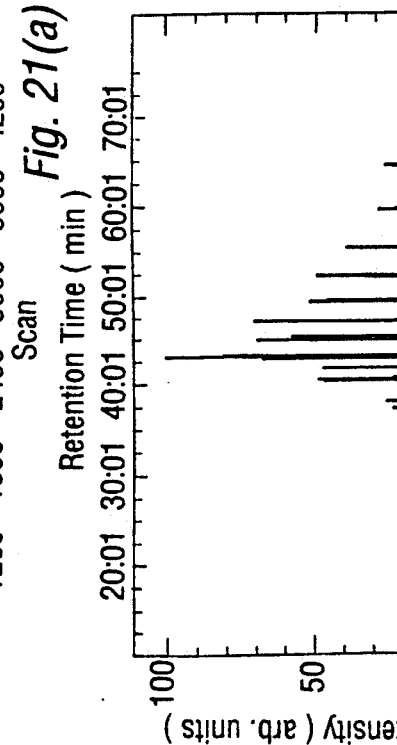

FIG. 20 shows spectra of control (PR3 plus culture medium) and the results of treatment with two different strains of modified microorganisms, modified *Acinetobacter calcoaceticus* (BNL-4-21) and modified *Arthrobacter* sp. (BNL-4-22). The results of gas chromatographic analysis performed in the same samples of untreated and treated PR3 crude oil are shown in FIGS. 21 and 22.

The extent of emulsification of PR3 by modified *Sulfalobus solfataricus* (BNL-TH-29) is small (spectrum 2, FIG. 18) when the oil is the sole carbon source, as compared to the extent of emulsification where the carbon source is oil plus yeast (spectrum 3, FIG. 18). In comparison, the action of modified *Acinetobacter cal-*

*coaceticus* (BNL-4-21) and modified *Arthrobacter* sp. (BNL-4-22) on PR3 as the sole carbon source is significant (FIG. 20, spectrums 2 and 3, respectively). The results of these experiments, expressed in terms of Klett units, are given in Table 4.

TABLE 4

| Salts | Klett Units |
|---|---|
| PR3 + medium (inorg. salts) | 10 |
| PR3 + medium (inorg. salts) + BNL-TH-29 | 30 |
| PR3 + medium (inorg. salts + yeast extract) + BNL-TH-29 | 150 |
| PR3 + medium (inorg. salts) + BNL-4-21 | 50 |
| PR3 + medium (inorg. salts) + BNL-4-22 | 200 |

Figure 23:
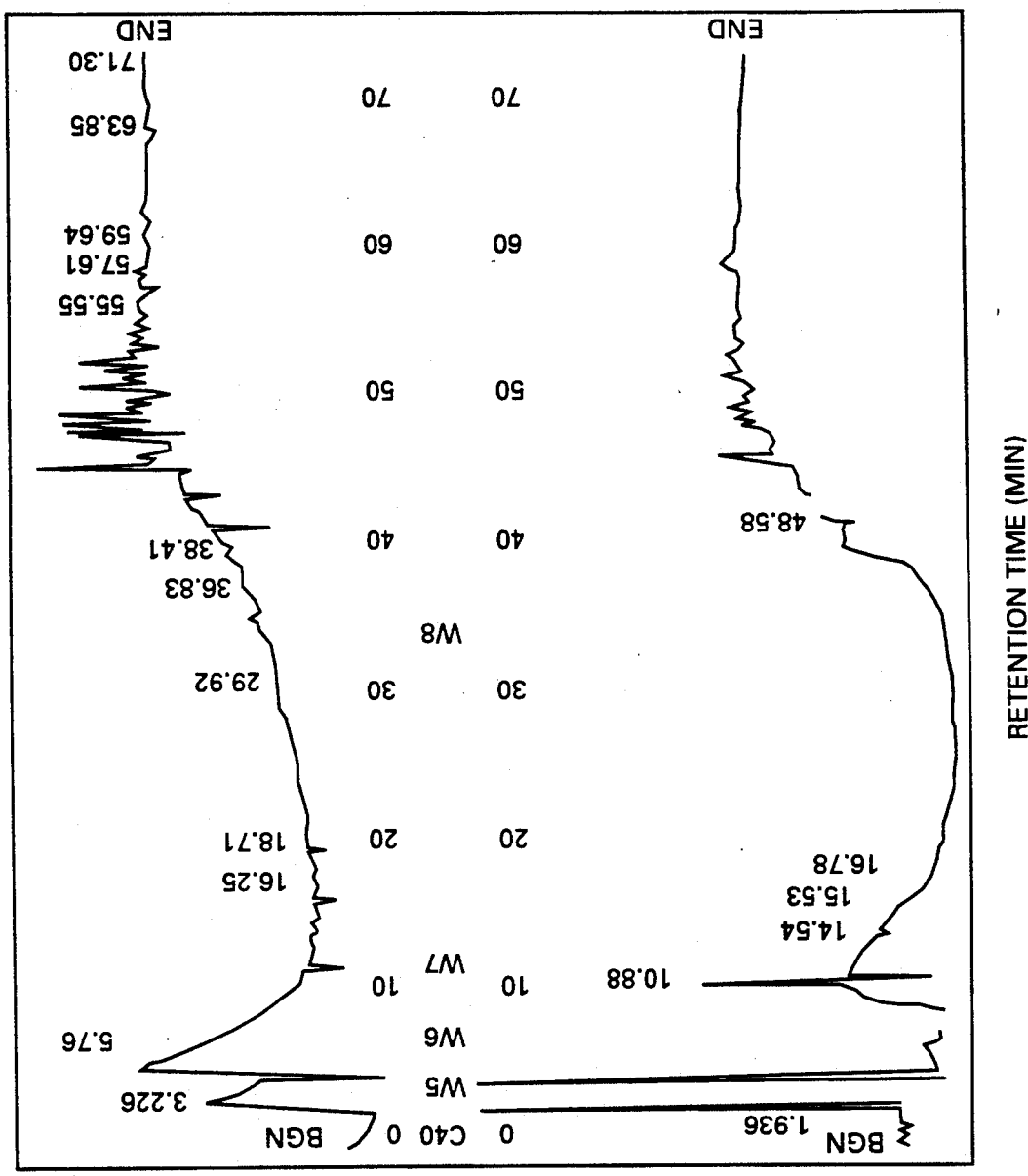
FIG. 23 shows GC/FPD sulfur traces for PR3 (a) before treatment, and (b) after biotreatment with (BNL-4-24).
Figure 24:
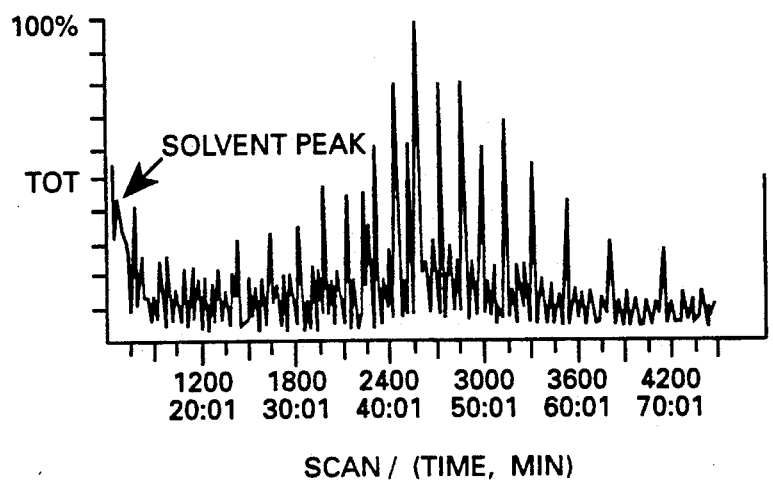
FIG. 24 shows GC/MS traces of the PR3 corresponding to the sulfur compounds (C) before treatment (control), (D) PR3 treated in the medium and under identical conditions but without inoculation with Bacteria, and (E) PR3 after biotreatment with BNL-4-24.
Figure 24:
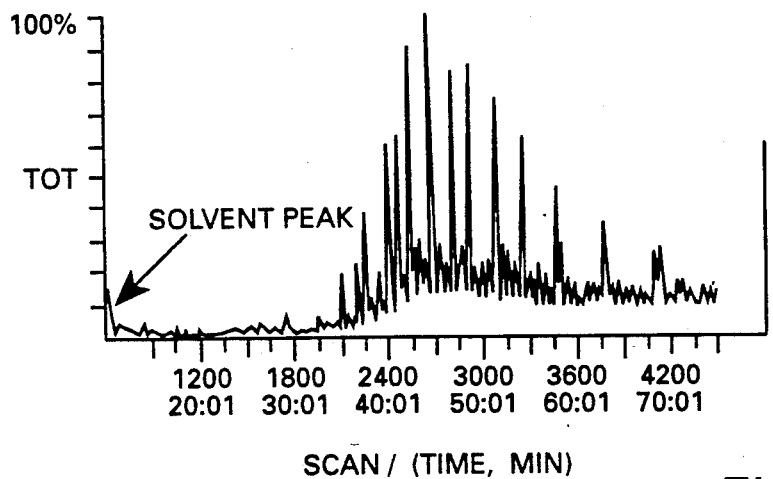
Figure 24:
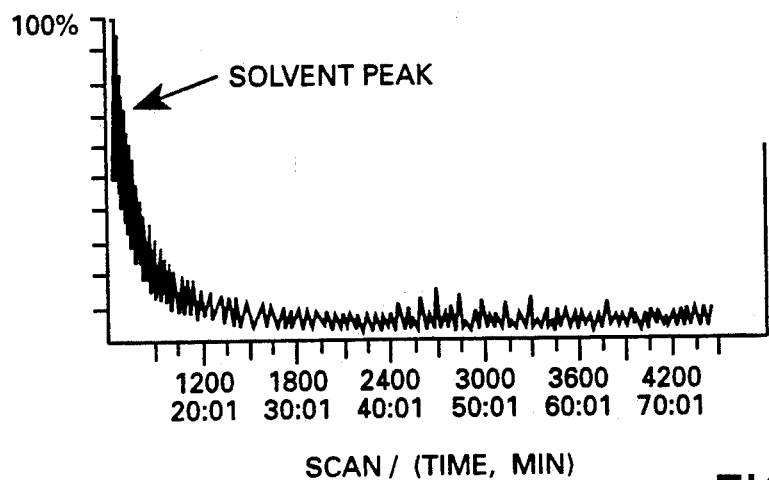

The gas chromatographic analysis of PR3 biotreated with modified *Acineobacter calcoaceticus* (BNL-4-21) and modified *Arthrobacter* sp. (BNL-4-22) are given in FIGS. 23 and 24, respectively. In both figures, the treated and untreated PR3 shows significant differences. In a lower range, these changes occur in the alkane and monoaromatic fractions representing low molecular weights. With increase in molecular weight, there are changes in the naphthalene fractions, followed by changes in mono- and tri- aromatized styrene fractions, all of which represent high molecular weight fractions. Thus, as illustrated in FIGS. 23 and 24, in the 800 to 2400 scan range there is a major change in the PR3 composition after treatment with either of the modified microorganisms. In the 2400–4200 scan range, i.e. in the area of higher molecular weight components of the crude, there are significant quantitative changes. In both samples, the duration of biotreatment was three weeks. A peak-by-peak comparison of relative intensities in the 2400–4200 scan region of both figures suggests that modified *Arthrobacter* sp. (BNL-4-22) caused a larger alteration in the heavy end of the crudes. This result is consistent with the earlier observations expressed in Klett units, as illustrated in Table 4 which were performed under identical experimental conditions. These results indicate a difference in the effect of biotreatment by two different modified microbial strains on the same oil, particularly in the extent of biochemical alteration of the oil when it was used as a sole carbon source during biotreatment.

Example 7 a) Several crude oils were incubated with two species of bacteria, modified in accordance with the present invention, over a period of two months and the viscosity of the produced emulsions were then measured with an LVT viscometer at 25° C. The results are shown in Table 5. Variations in viscosity are consistent with the Examples 6 and 7 showing microbial species-oil type dependencies.

TABLE 5

| | Viscosity in Centipoises | |
|---|---|---|
| | BNL-4-26 | BNL-4-25 |
| Prudhoe Bay (Alaska) | 3.9 | 5.2 |
| Naval Petroleum Reserve PR3 (Wyoming) | 5.3 | 4.0 |
| Wilmington (California) | 3.5 | 3.7 | b) Naval Petroleum Reserve (PR3) was treated with four different types of bacteria under identical experimental conditions. The produced oil emulsions containing the oil were then extracted with methylene chloride and the solvent removed by evaporation. Results are shown in Table 6, both in terms of Klett units and grams of oil per liter of emulsions produced.

TABLE 6

| Klett Units | Microbial Strain | Oil Content in Emulsion (g/l) |
|---|---|---|
| 50 | BNL-4-21 | 3.58 |
| 200 | BNL-4-22 | 11.0 |
| 700 | BNL-4-23 | 18.0 |
| 30 | BNL-4-24 | 3.03 |

Figure 25:
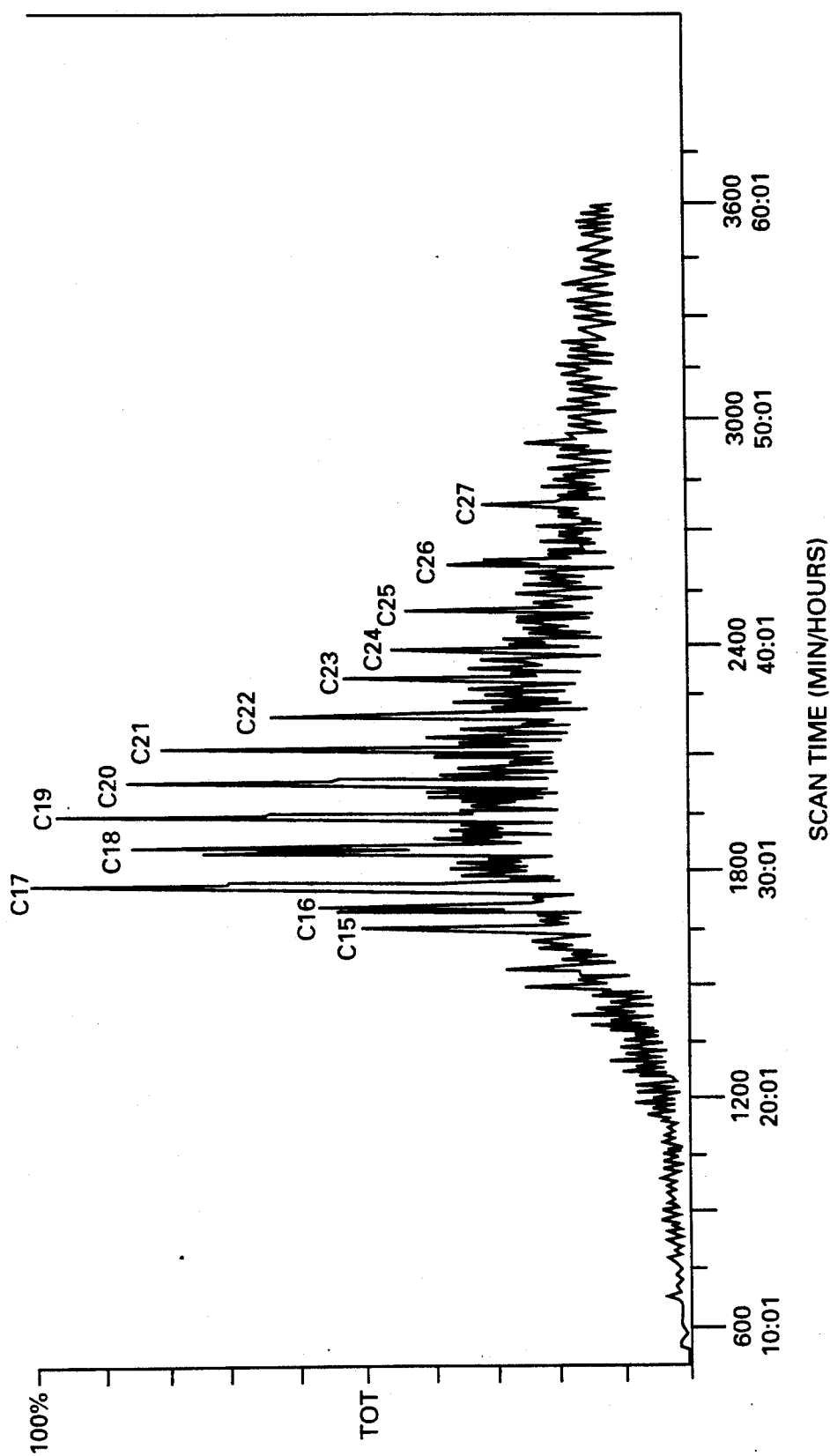
FIG. 25 is a GC Trace of Biotreated and Extracted Emulsified Oil.
Figure 26:
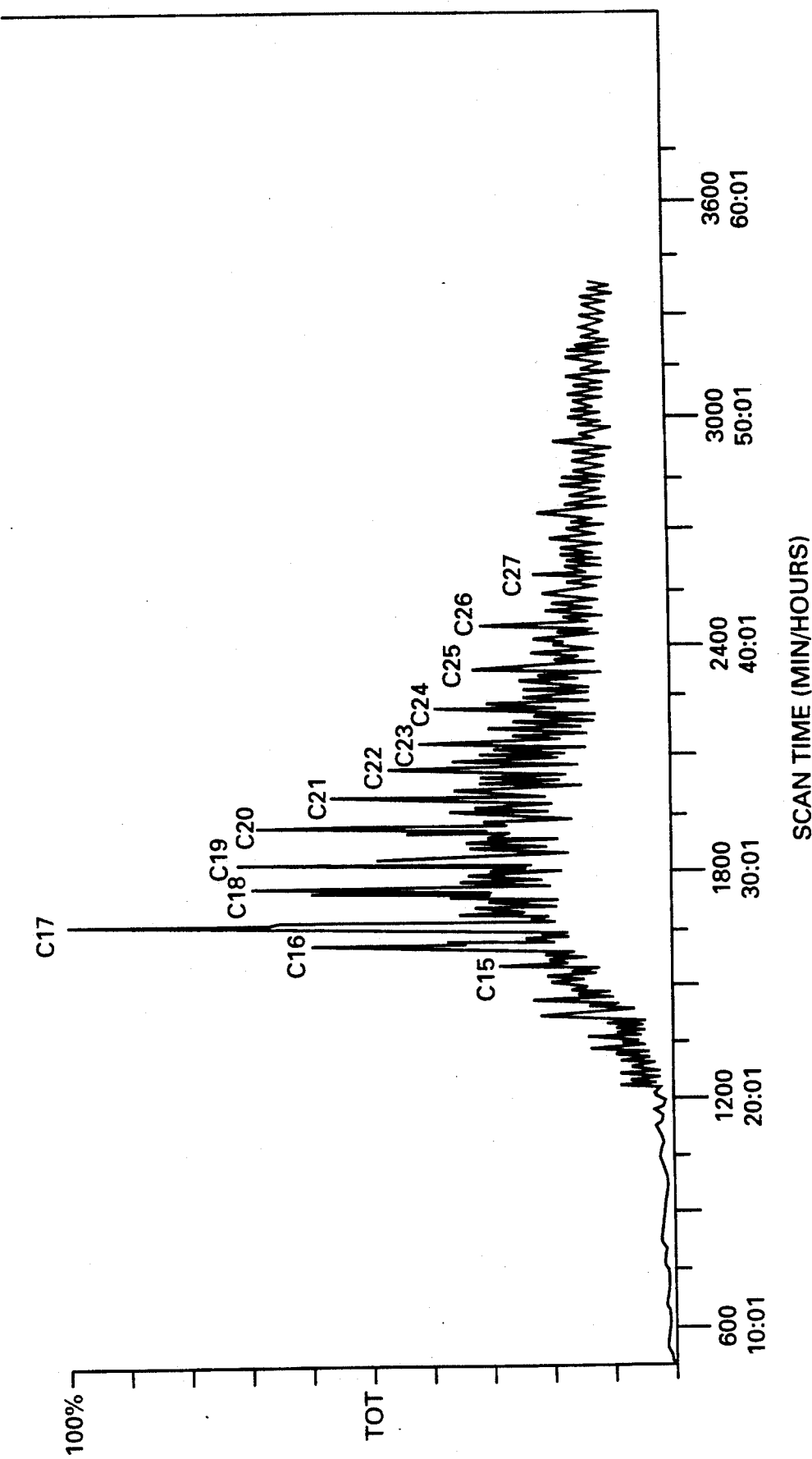
FIG. 26 is a GC Trace of Control (non-treated extracted oil).

The results summarized in Table 6 show a marked bacterial species dependence on the amount and the extent of emulsification. Gas Chromatography-Mass Spectrometry comparison of BNL-4-23 treated oil in emulsion and control (aqueous phase+nutrients+oil only) shows that C-15 to C-27 hydrocarbons have been emulsified, as shown in FIGS. 25 and 26. It is to be understood that there is some loss of <C-15 hydrocarbons due to evaporation step in the extraction procedure.

Changes in the Composition of Sulfur Containing Fractions of Biotreated crudes

EXAMPLE 8

In this example, particular attention is given to changes in the composition of sulfur compounds which occurs due to the biotreatment described in Examples 1 and 2. For this purpose, the Perkin/Elmer 8700/ITD System was equipped with a splitter, which allows a portion of the sample to be analyzed by the Gas Chromatograph (GC) and the Flame Photometric Detector (FPD). This system was specifically used for detecting sulfur. This capability made it possible to follow changes in the chemical composition of sulfur containing compounds caused by the microbial treatment.

Figure 27:
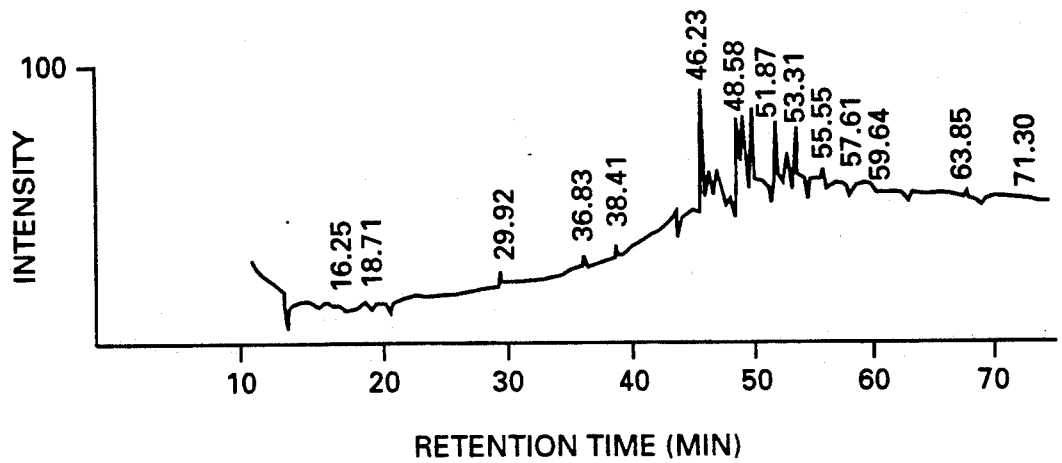
FIG. 27 shows the GC/FPD sulfur trace of BNL-4-24 treated with PR3 (a) before treatment, and (b) after treatment [injected (2μl)].
Figure 27:
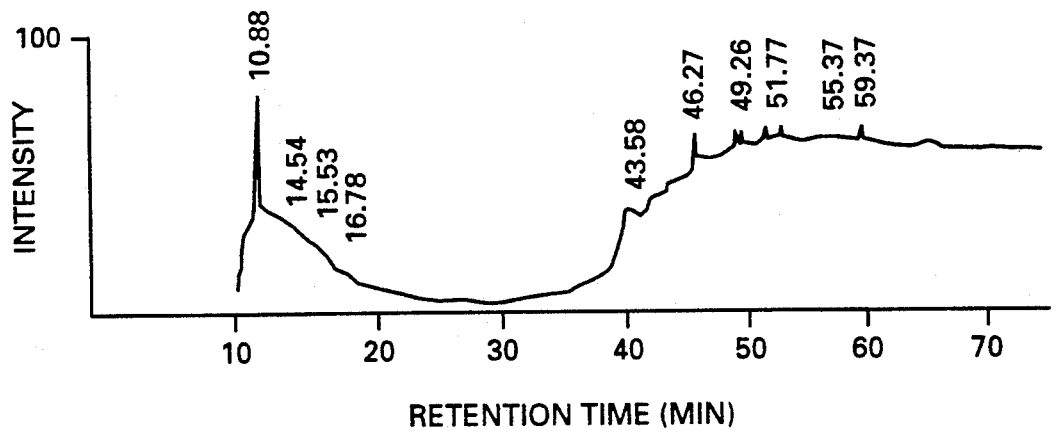

PR3 was treated with modified *Pseudomonas* sp. (BNL-4-24) as described in Examples 1 and 2 at a temperature of 65°–70° C. and a pressure of 1400 p.s.i. for three weeks. This treatment resulted in considerable changes in the composition of the sulfur compounds in the crude oil indicating the decomposition of sulfur containing compounds in the crude oil. The GC/PFD sulfur trace of PR3 illustrated in FIG. 27 shows considerable qualitative and quantitative changes in the sulfur trace.

Example 9

Two higher sulfur containing oils were subjected to biotreatment following the process described in Examples 1 and 2. Changes in the total sulfur contents of two Venezuelan crudes are presented in Table 7.

TABLE 7

Total sulfur content of Boscan and Cerro Negro Venezuelan crude oils before and after biotreatment.

| Oil | Total % Sulfur | % Loss |
|---|---|---|
| Untreated Boscan | 5.49 | — |
| Boscan treated with BNL-4-22 | 4.14 | −25 |
| Boscan treated with BNL-4-23 | 4.84 | −11 |
| Boscan treated with BNL-4-24 | 4.92 | −10 |
| Untreated Cerro Negro | 4.37 | — |
| Cerro Negro treated with BNL-4-24 | 3.10 | −29 |
| Cerro Negro treated with BNL-4-23 | 3.74 | −25 |
| Cerro Negro treated with BNL-4-22 | 3.21 | −27 |

Figure 28:
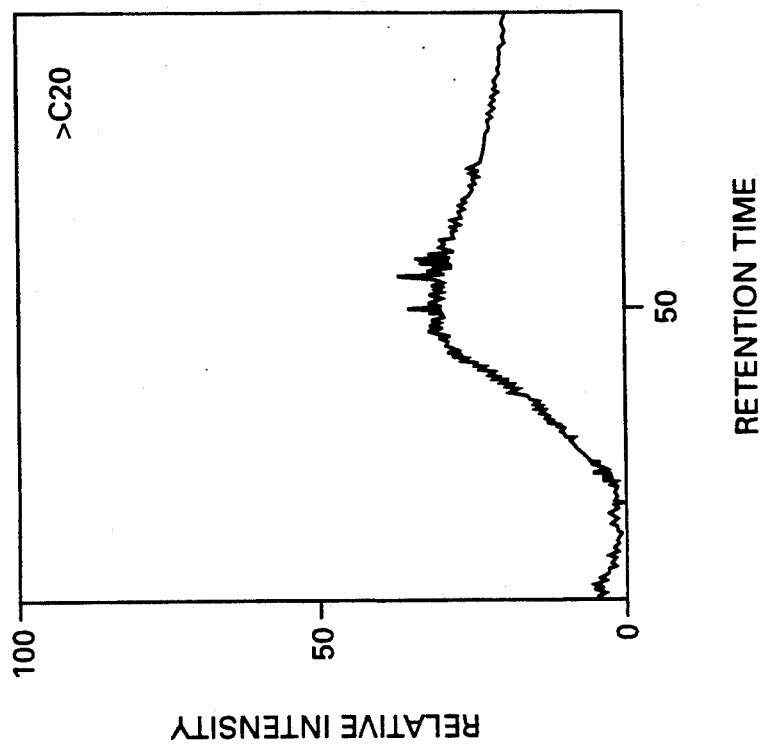
FIG. 28 shows the FPD trace of (a) Cerro Negro crude (2 μl injection ⅛ split); and (b) Cerro Negro crude treated with BNL-4-24, under identical conditions.
Figure 28:
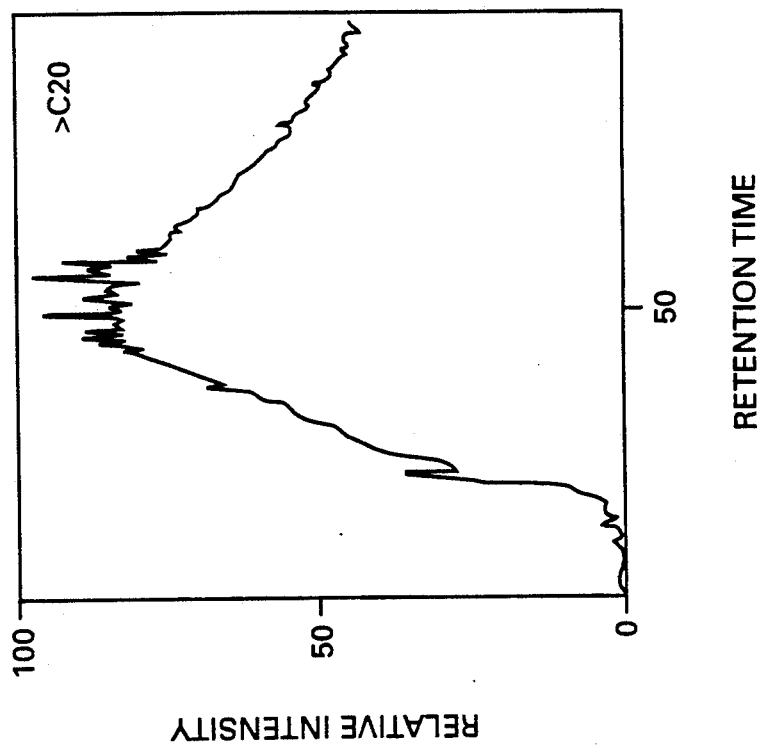

Significant decrease in sulfur content is evident in Table 7. In FIG. 28, GC/FPD scans for untreated and treated Cerro Negro oil are shown. In both cases identical experimental conditions have been used. Treatment of Cerro Negro crude with BNL-4-24 resulted in an almost 50% decrease in sulfur-containing compounds in the region containing <C20 fractions.

Example 10

Figure 29:
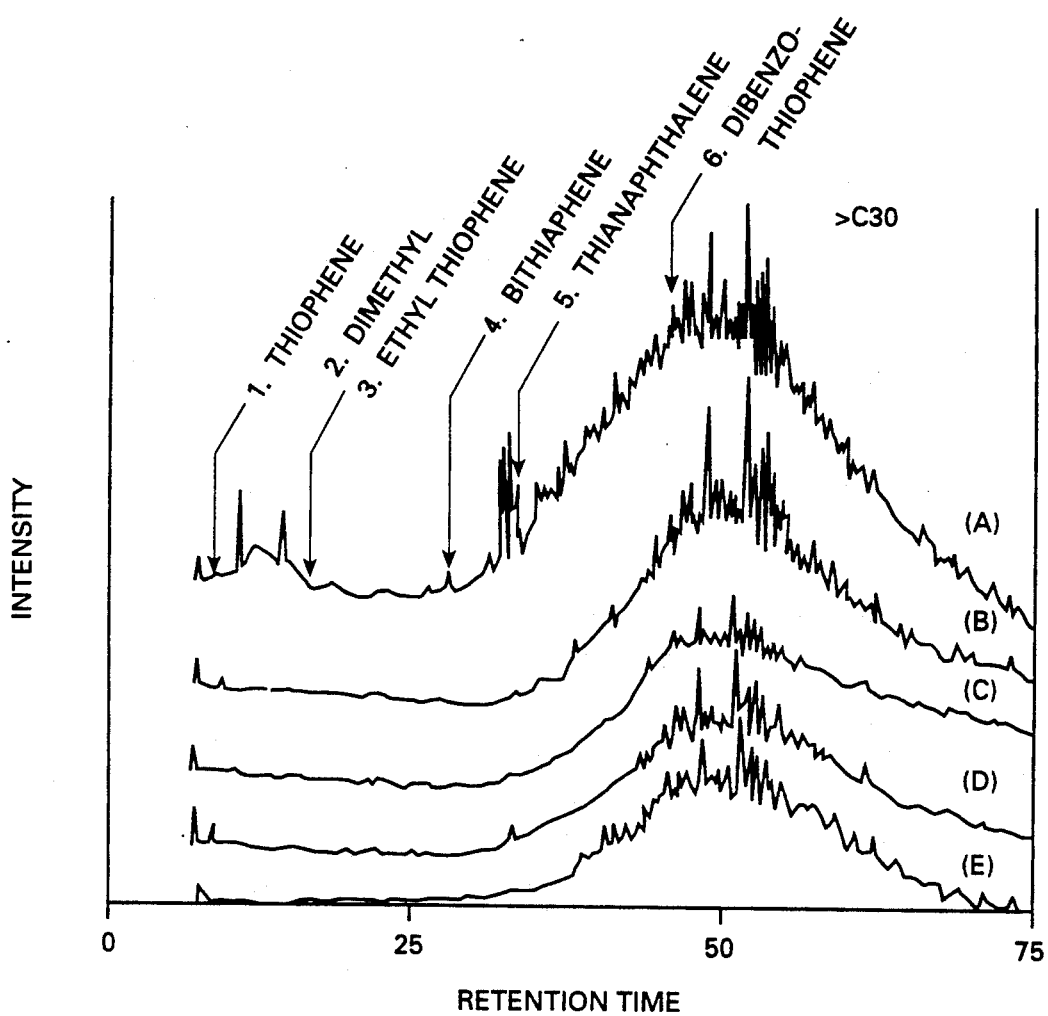
FIG. 29 shows FPD traces of Cerro Negro crude treated and processed under identical conditions. The data are for <C30 range of compounds.

Biotreatment of Cerro Negro crude was carried out with several different strains of microorganism under identical experimental conditions, as described in Examples 1 and 2. FIG. 29 shows FPD traces for <C30 range of compounds of the cerro Negro crude: (a) untreated; (b) treated with BNL-4-21; (c) treated with BNL-4-24; (d) treated with BNL-4-23; and (e) treated with BNL-4-22. The results shown in FIG. 29 indicate that while there is an overall similarity in the decrease in the concentrations of organic sulfur compounds, there may also exist fine structural differentiation depending on which particular microbial species has been used. These are the first comparative sets of data showing biochemical modification and/or degradation of organic sulfur-containing compounds characterized by molecular markers ranging from thiophene to dibenzothiophene.

Example 11

The results obtained in Example 9 on the biotreatment of Boscan Venezuelan crude show that BNL-4-22 removed 25% of original sulfur present. Thus, BNL-4-22 appeared to be more efficient in removing sulfur than the other two strains tested, which removed 10% and 11%, respectively. For the purpose of this Example, the BNL-4-22 biotreatment of Boscan was assumed to be the more efficient and was, therefore, chosen for following detailed gas chromatographic (GC) analysis.

Figure 30:
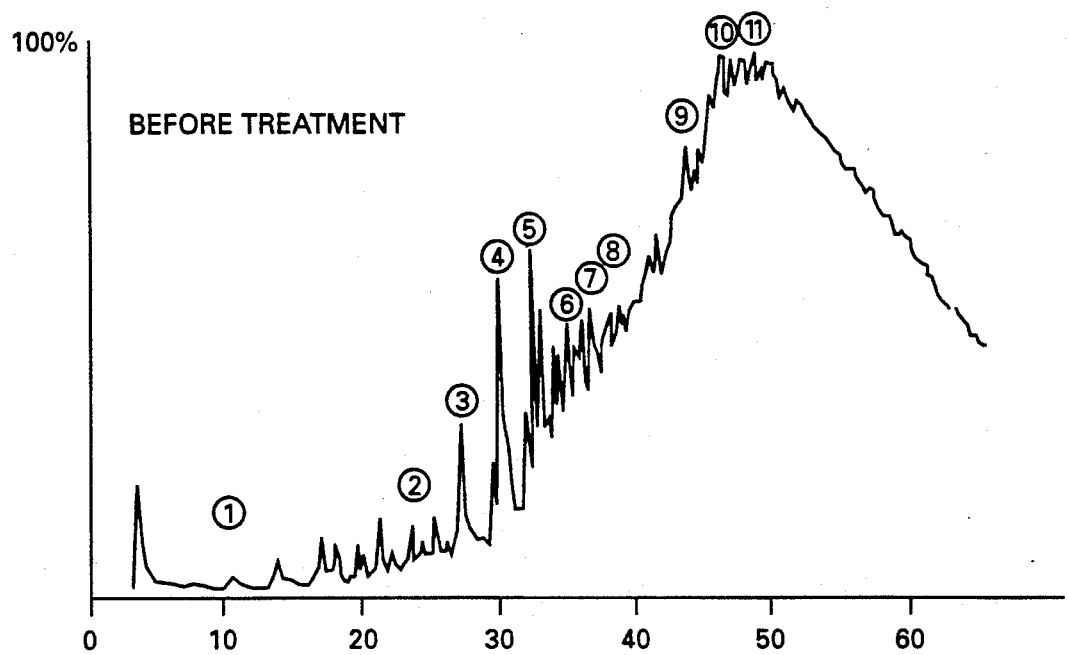
FIG. 30 shows FPD traces of Boscan Oil: (A) before, and (B) after the Biotreatment with BNL-4-22.
Figure 30:
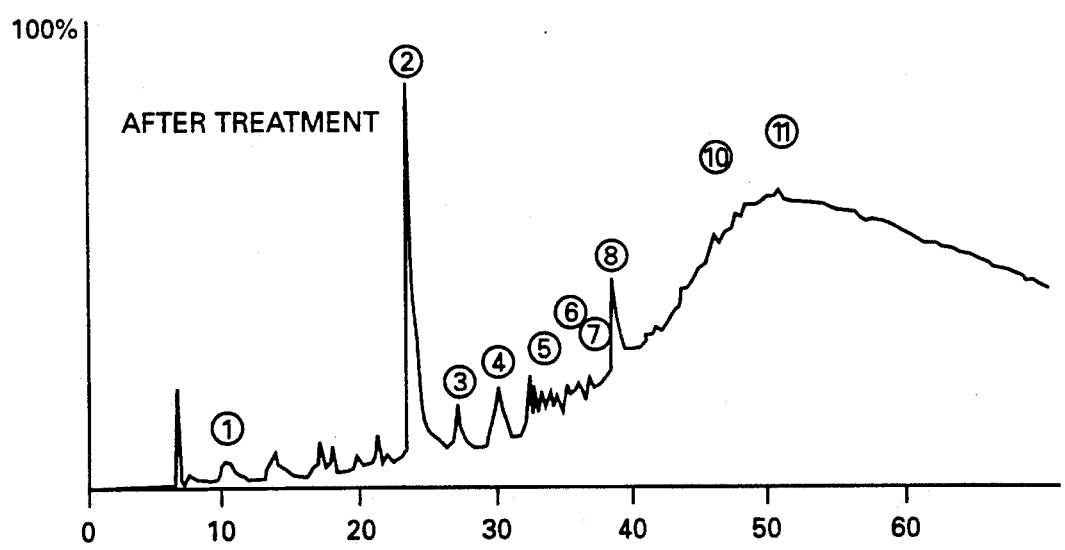

Traces of gas chromatograms in which flame photometric detector (FPD) specific for sulfur has been used are shown in FIG. 30. FIG. 30A shows the organic sulfur compound distribution in the sample of the Boscan crude before microbial treatment with BNL-4-22, while FIG. 30B shows the same trace after biotreatment with BNL-4-22. It is to be understood that in this Example, before treatment means, sample treated under identical experimental conditions (control sample), including the culture medium without microorganism; while after treatment, means identical experiment, however, in the presence of microorganisms. The GC peaks are identified in Table 8, in which each sulfur containing heterocyclic compound represents a characteristic molecular marker for a group of isomeric organic sulfur compounds. For the purposes of comparison both chromatograms have been plotted on the same scale.

TABLE 8

| | Organic Sulfur Compounds Molecular Markers | |
|---|---|---|
| GC Peak No. | Atomic Composition | Compound |
| 1 | $C_7H_9S$ | C2-thiophene |
| 2 | $C_8H_6S$ | Thianaphthalene |
| 3 | $C_9H_8S$ | C1-thianaphthalene |
| 4 | $C_{10}H_{10}S$ | C2-thianaphthalene |
| 5 | $C_{11}H_{12}S$ | C3-thianaphthalene |
| 6 | $C_{12}H_{14}S$ | C4-thianaphthalene |
| 7 | $C_{13}H_{16}S$ or higher analogous | C5-thianaphthalene |
| 8 | $C_{12}H_8S$ | dibenzothiaphene |
| 9 | $C_{14}H_8S$ | C2-dibenzothiaphene |
| 10 | $C_{15}H_{10}S$ | Methylphenantro [4,5-b,c,d]thiophene |
| 11 | $C_{16}H_{10}S$ | Benzonaphthothiaphen isomers |

The results indicate that during the biotreatment an overall decrease in the concentration of higher molecular weight compounds has occurred. This is marked by a substantial decrease in the concentration of methyl phenanthrothiophenes and benzonaphthothiophenes, and disappearance of C2-dibenzothiophenes (or their analogues). There are changes in the concentration of dibenzothiophene type compounds, an apparent disappearance of C5 and C4-thianaphthalenes, a lowering in C3-thianaphthalenes, as well as considerable decrease in C1 and C2-thianaphthalenes. There is an increase in the concentration of thianaphthalene and apparently small change in the concentration C2-thiophene. This experimental evidence indicates that during the action of BNL-4-22 on the Boscan crude, active biochemical processes tend to decrease the overall concentration of the heavier, i.e., C11 to C16 organic thiophene type sulfur compounds, decompose some C7, C9 and C10, and interestingly increase the concentration of the C8 thianaphthalene. (peak 2)

Example 12

An analytical tool exceptionally useful to follow total changes in sulfur compounds present in crude oils is the XANES analyses. Results of comparative analyses by XANES of Boscan and Cerro Negro crude oils are shown in Table 9.

TABLE 9

| XANES analysis of sulfides, thiophenes and sulfoxide contents of untreated and treated crude oils | | | | | |
|---|---|---|---|---|---|
| Crude Oil | Micro-organisms | Bio-treatment | Relative Content | | |
| | | | Sulfide | Thiophene | Sulfoxide |
| Boscan | 0 | untreated | 0.198 | 0.738 | 0.064 |
| | BNL-4-22 | treated | 0.159 | 0.655 | 0.186 |
| | BNL-4-23 | treated | 0.121 | 0.743 | 0.135 |
| Cerro Negro | 0 | untreated | 0.147 | 0.781 | 0.072 |
| | BNL-4-22 | treated | 0.179 | 0.683 | 0.138 |
| | BNL-4-23 | treated | 0.103 | 0.713 | 0.184 |

The results shown in Table 9 suggest that the biotreatment decreases the sulfide and thiophene contents of the crudes and increases the sulfoxide contents. Since volatile products from biotreatment containing sulfur have not been detected to date, and there is a detected decrease in sulfur, a possible interpretation of these results is that the products are soluble in the water phase that is always present in the culture medium. A logical extension of these results is that some of the products may be water soluble sulfones responsible for the concurrent emulsification of the oil.

Changes in the Chemical Composition of crudes

EXAMPLE 13

Examples 1-3 show that the composition of organic compounds present in crude oils changes during a biotreatment in favor of lighter components. The implication of these observations may be that the biotreatment favors formation of a lighter "solvent" richer chemical composition of oil.

To further explore and/or verify this hypothesis a diagnostic molecular marker analysis of the untreated and treated Boscan crude was carried out. Diagnostic molecular marker analysis is an analytical technique which uses characteristic masses generated during fragmentation of organic molecules in a mass spectrometer; as described by Williams, et al., in "Biodegradation of South Texas Eocene Oils—Effects on Aromatics and Biomarkers." Leythauser and Rullkøtter (Eds.), *Part I*, Petroleum Geochemistry, 451–461 Pergamon Press, U.K., 1985.

Figure 31:
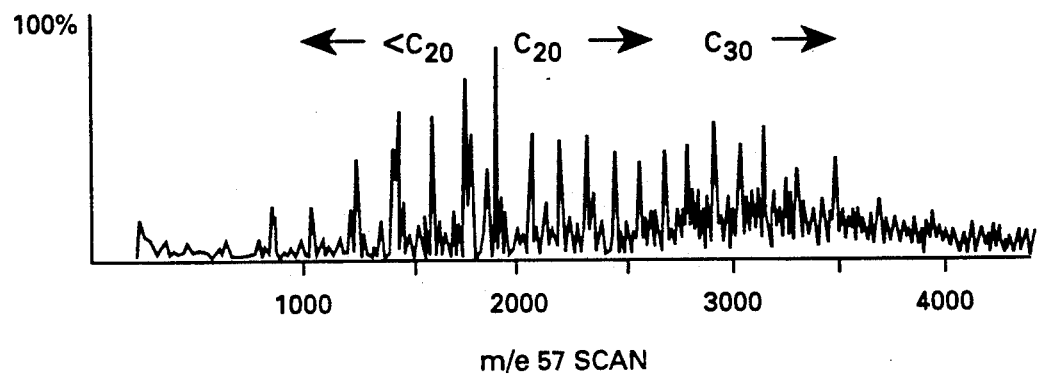
FIG. 31 is an m/e 57 scan of the aromatic fraction of Boscan Crude: (A) before treatment, and (B) after the treatment with BNL-4-22.
Figure 31:
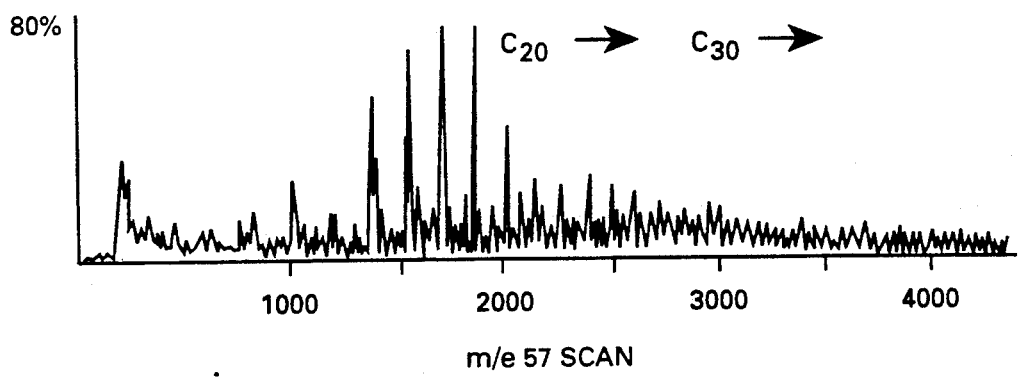
Figure 32:
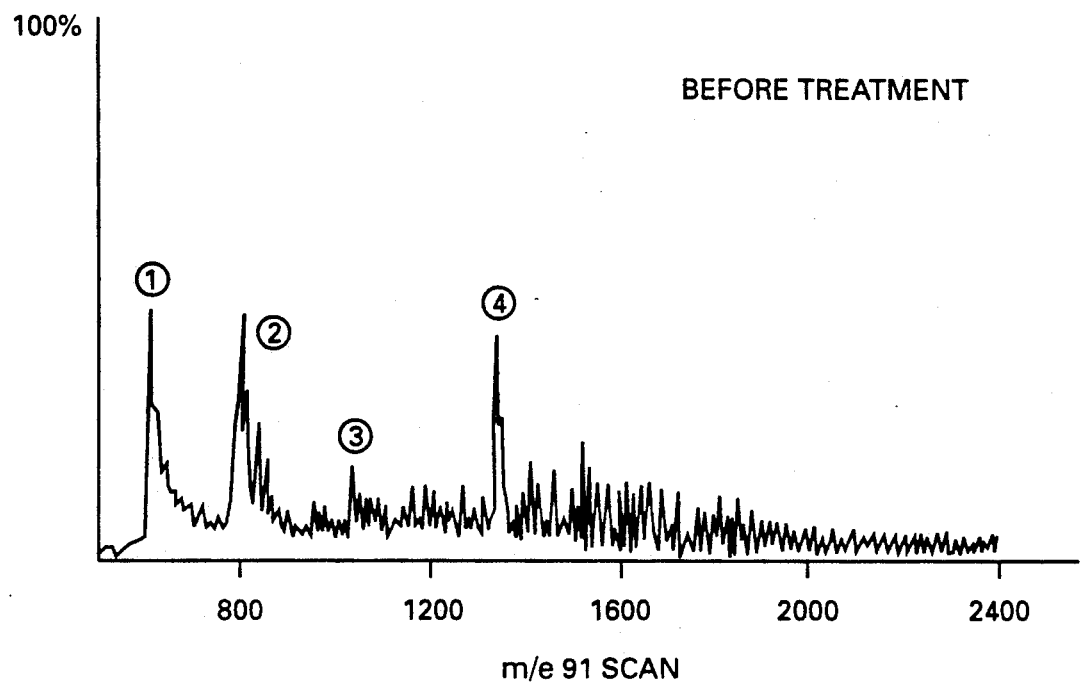
FIG. 32 is an m/e 91 Scan of the aromatic fraction of Boscan Crude: (A) before treatment, and (B) after the treatment with BNL-4-22. Legend: 1 Toluene; 2 C2-Benzene; 3 C3-Benzene, and 4 Naphthalene.
Figure 32:
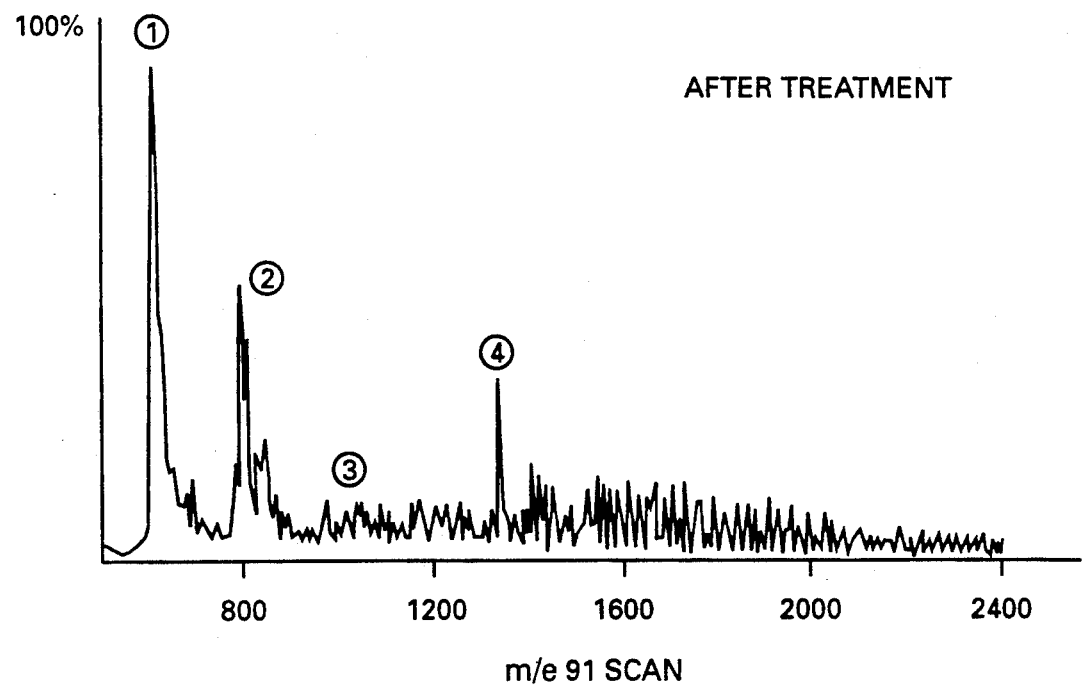

The biotreatment of Boscan crude with BNL-4-22 cause a substantial reduction in the C20 to C30 alkanes and an increase in the concentration of the <C20 type alkanes as shown in FIG. 31. The m/e 57 diagnostic molecular marker used in this Example is characteristic of lower molecular weight alkanes. Corresponding analysis using m/e 91, characteristic for substituted aromatics is shown in FIG. 32. The results are complimentary to those for alkanes: biotreatment causes an increase in the concentration of toluene and the C2-benzene and a decrease in larger, i.e., naphthalene type organic compounds.

The changes in the chemical composition of Boscan crude brought about by the biotreatment of the crude are consistent with those observed for Cerro Negro, eg. in Example 10. However, they differ in chemical detail, and further indicate the significance of microbial species/crude oil type variety of interactions. These observations also imply that the biochemical mechanisms may differ with microbial species and/or types of crude oils being biotreated.

Effects of Biotreatment on the Composition of Metal Complexes in Crude Oils

Example 14

Figure 33:
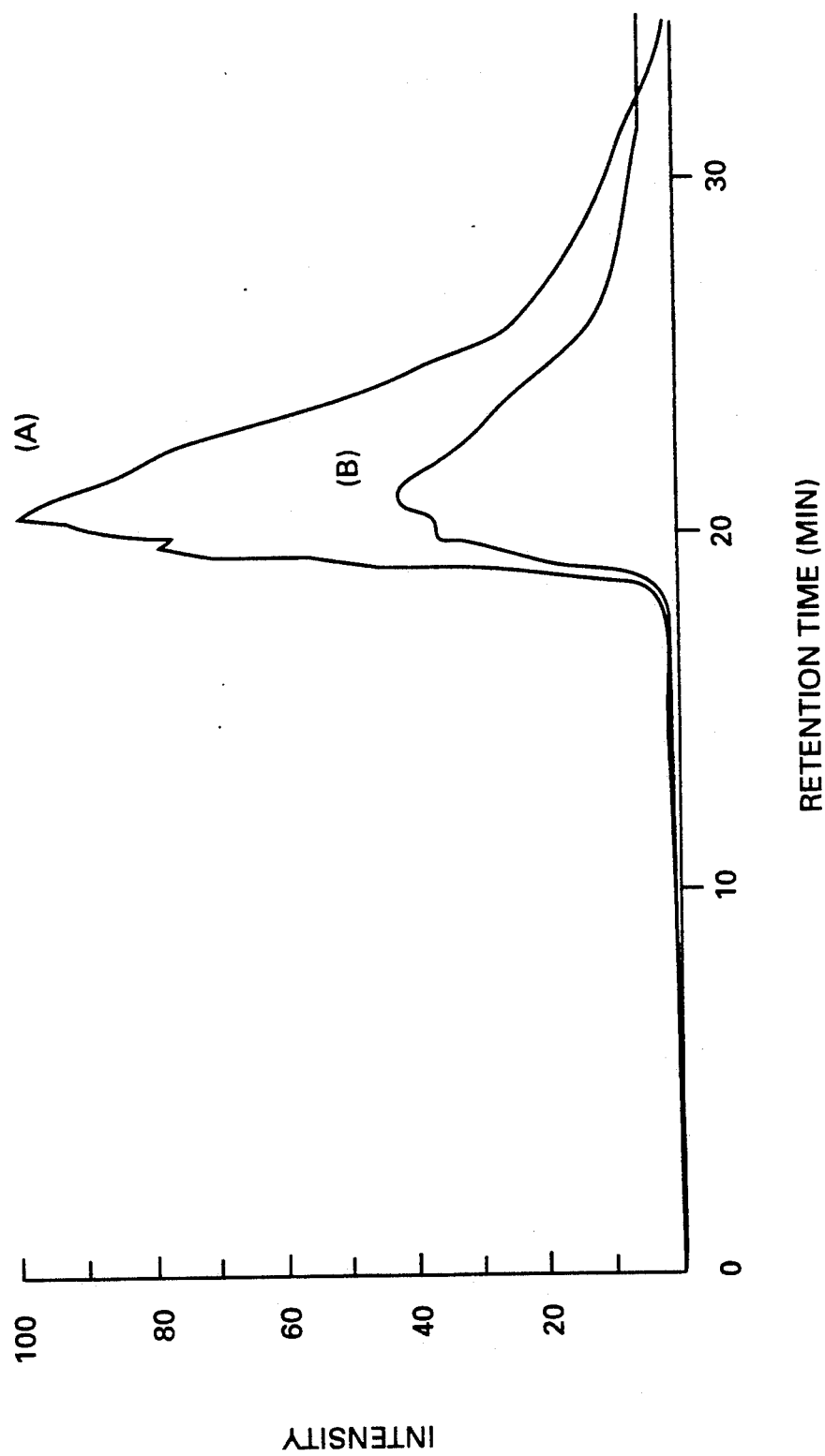
FIG. 33 shows reduction of nickel porphyrin content in Wilmington, Calif., crude (a) before treatment, and (b) after treatment with BNL-4-22.

Chemical and concentration changes of metal complexes present in crude oils also occur as a result of biotreatment. In order to test for chemical changes in the composition of metal complexes, several experiments were conducted. In all cases, analyses were carried out using a gas chromatograph with an atomic emission detector (GCAED) (Hewlett-Packard Gas Chromatography with Atomic Emission Detector-Factory Specified Procedure. In this analytical technique, the metals are detected selectively in the gas chromatograph by their specific emission wavelength, appropriate calibration allows the determination of metal species. Biotreatment of Wilmington, Calif. crude with BNL-4-22 resulted in a considerable reduction of nickel porphyrin complex as shown in FIG. 33. In this analysis the GC system was calibrated with nickel octaethyl porphyrin eluting at 18.5 mins and cobaltoctaethyl porphyrin eluting at 19.1 mins. FIG. 33 evidences the removal of a trace metal from a crude oil by means of biotreatment.

Figure 34:
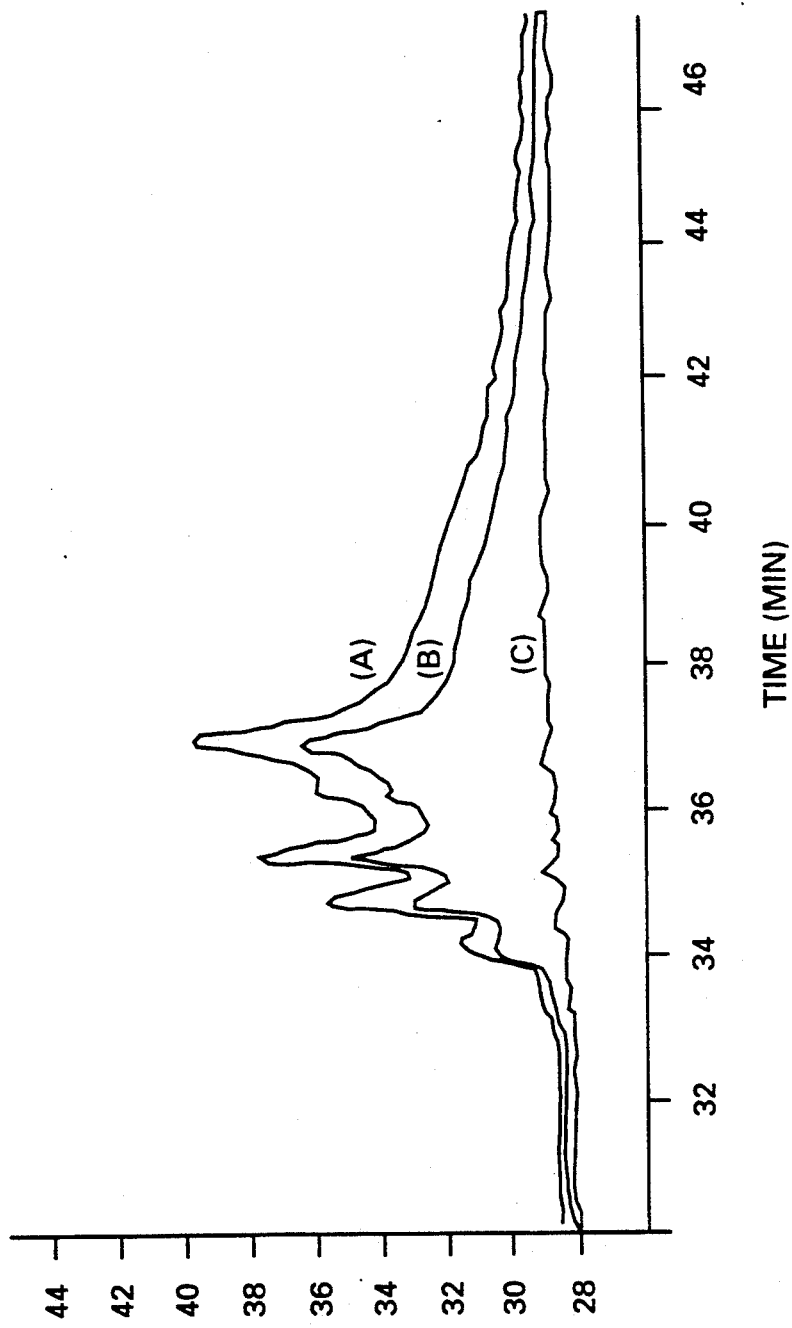
FIG. 34 shows the GCAED trace of Wilmington, Calif., crude (a) untreated; (b) treated with BNL-3-25; and (c) treated with BNL-4-25.

Another sample of Wilmington, Calif. crude oil was treated with thermophiles and the results are shown in FIG. 34 (a) untreated; (b) treated with BNL-3-25; and (c) treated with BNL-4-25. The results shown in FIG. 34 indicate that biotreatment effects removal of trace metals and that there is a difference in the biochemistry when the same oil is treated by different microorganisms.

EXAMPLE 15

This Example was carried out in order to determine how many metals can be removed by processing of crude oils. To accomplish this, samples of biotreated and untreated crude oils were digested by nitric acid vapors, followed by dissolution in 1% aqueous nitric acid. The acid solutions were then analyzed by Induced Coupled Plasma Mass Spectrometry (ICP-MS) by VG Plasma Quad II Plus scan from 4 to 240 in accordance with VG Instruments recommended multielement scan method. The results for Cerro Negro biotreated with BNL-4-23 over a period of ten days are shown in Table 10.

TABLE 10

Changes in the selected trace metals contents of Cerro Negro oil treated with BNL-4-23.

| Metal | Metal Content µg/ml | |
|---|---|---|
| | Untreated | Treated |
| V | 3330 | 2290 |
| Ni | 926 | 639 |
| Mg | 78 | 6.8 |
| Sr | 9.6 | 1.7 |
| Mn | 15.8 | 1.8 |

These results indicate that other trace metals are also being removed in the same manner. However, because of the digestion method used, arsenic, selenium and mercury, may have been volatilized and therefore "lost" during the sample treatment. These results are very promising, particularly for application in downstream processing of crude oils.

Enhancement of Biotreatment by Pre-Emulsification of Crude Oils

Example 16

The results obtained in Examples 5-7, 10 an d12, suggest that different strains of microorganisms acting on the same oil interact differently, appear to be consistent and warrant additional experimentation. Accordingly, in this Example the biochemical effects caused by microbial treatment of crude oils are compared to those due to microorganisms with and without process enhancement.

Wilmington, California crude oil was biotreated with several microorganisms, BNL-4-21, BNL-4-22, BNL-4-23, BNL-4-24 and a control sample which did not include any microorganisms. The viscosity of the samples at the end of biotreatment in (cps), and the extent of emulsification was measured for each samples and the results are shown in Table 11.

TABLE 11

Microbial Treatment of Wilmington Crude

| Microorganism | Days incubated | Viscosity at the end of biotreatment in cps | Emulsion in Klett units |
|---|---|---|---|
| BNL-4-21 | 20 | 3.6 | 180 |
| BNL-4-22 | 20 | 3.0 | 400 |
| BNL-4-23 | 23 | 3.0 | 180 |
| BNL-4-24 | 30 | 3.6 | 55 |
| Control | 55 | 3.3 | 7.5 |

Figure 35:
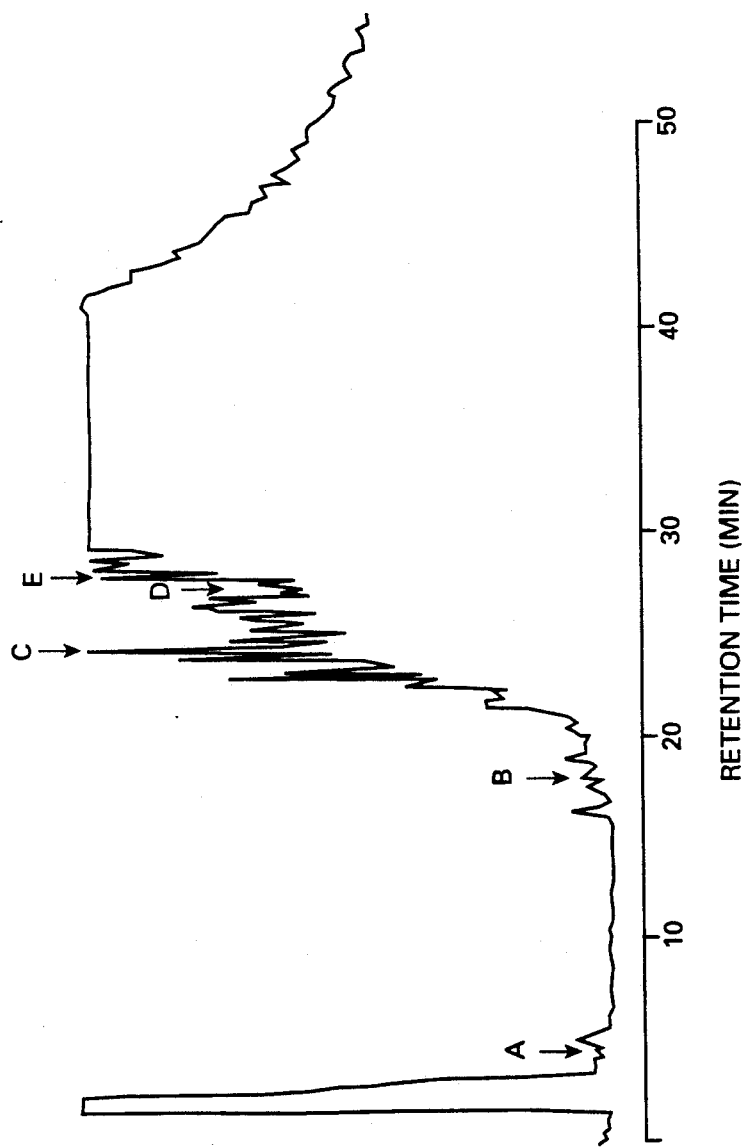
FIG. 35 is a Gas Chromatography-Flame Photoemission Detector (GCFPD) trace of untreated Wilmington, Calif. crude (sulfur specific trace). Molecular Markers A: Thiophene; B: Benzothiophene; C: Phenyl Sulfide; D: Dibenzothiophene; E: C-1 Dibenzothiophene.
Figure 36:
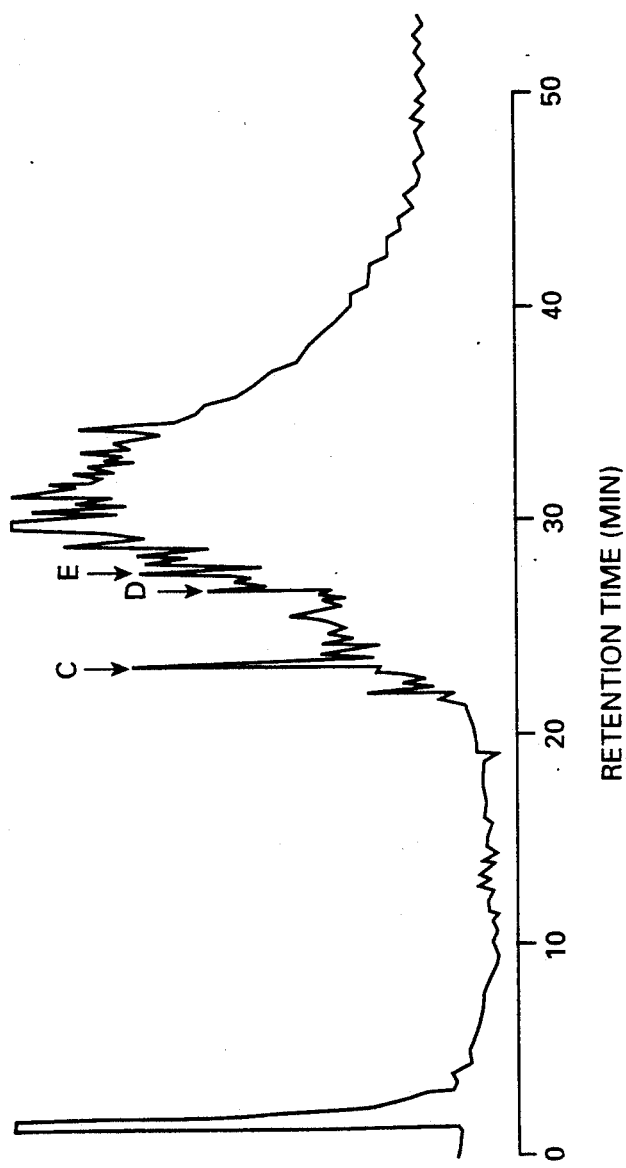
FIG. 36 is a GCFPD trace of Wilmington, Calif., crude biotreated with BNL-4-21. C,D, as in FIG. 35.
Figure 37:
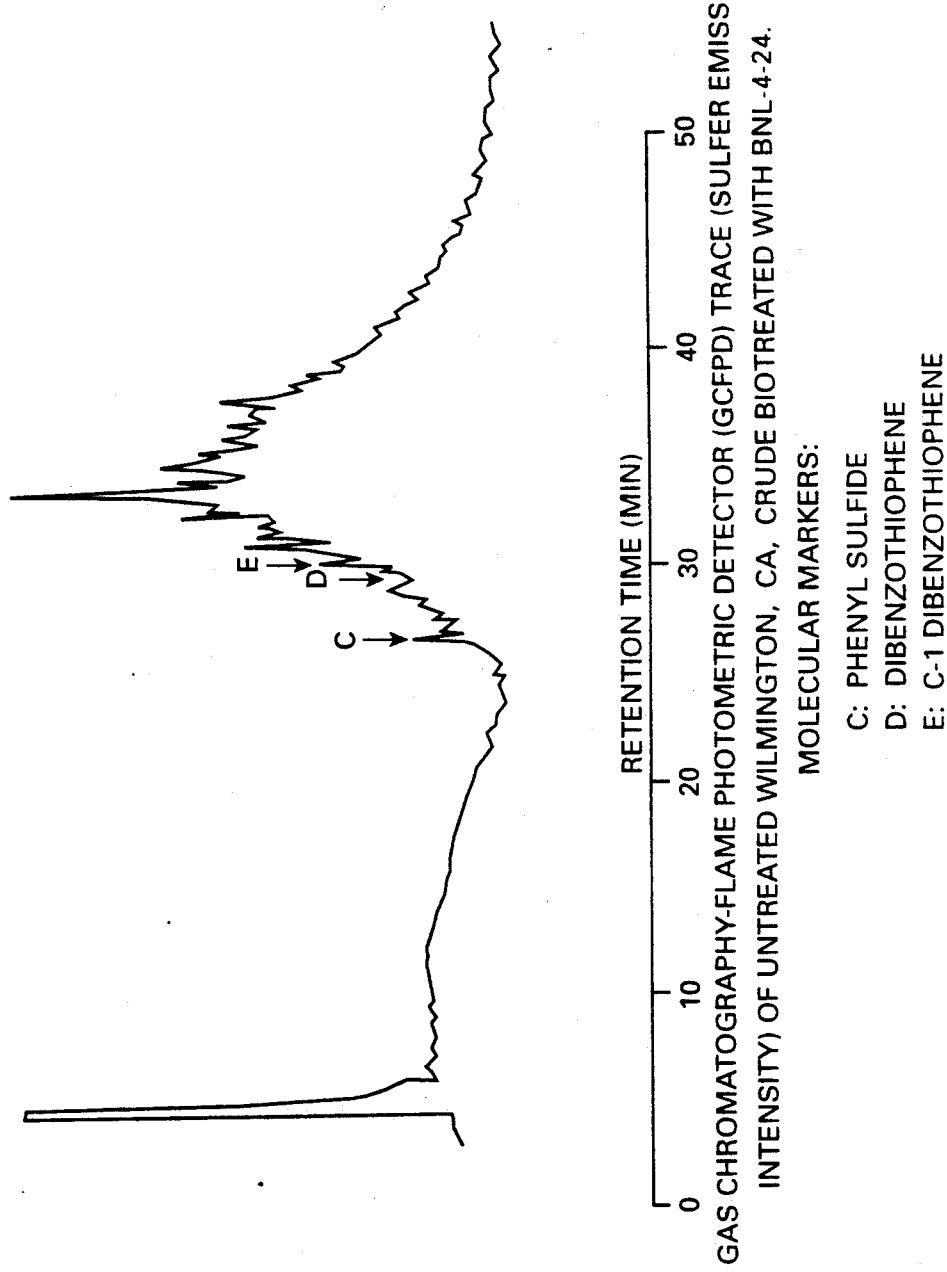
FIG. 37 is a GCFPD trace of Wilmington, Calif., crude biotreated with BNL-4-24. C,D, as in FIG. 35.

As shown in Table 11, BNL-4-24 is not the best emulsion producer. However, the results of Gas Chromatography-Flame Photoemission Detector (GCFPD) traces of the control and two (2) samples of biotreated (BNL-4-21 and BNL-4-24) Wilmington crude shown in FIGS. 35, 36 and 37, respectively, provide evidence that BNL-4-24 is highly efficient in conversion of organic sulfur compounds. In these figures the following letters indicate the molecular markers for A: Thiophane; B: Benzothiophane; C: Phenyl sulfide; D: Dibenzothiophane; and E: C-1 Dibenzothiophane. All gas chromatographic traces are on the same scale and run under identical conditions. It is interesting to note, as shown in Examples 5 at Table 3, that the same organism used in this experiment, when acting on heavy fractions (200° C. fraction) of Wilmington crude oil, produced a larger extent of emulsification than when acting on the whole crude oil.

EXAMPLE 17

It has been observed in carrying out Examples 5-7, 10, 12 and 16 that is some instances thermophilic microorganisms react with crude oils in a manner which causes the crude to be more efficiently emulsified. This information implies that chemically different emulsifying agents may be produced and further, the yields of naturally produced emulsifying agents may also vary as a function of microbial species and the chemical composition of oils. If this is true, then some microbial species may be more suitable as producers of surface active agents while others may be better biochemical processors of crudes. Consortium of such organisms may enhance the overall effect.

In order to test the "enhancement effect" a sample of the Wilmington crude oil was emulsified with "TERGITOL" (a commercial emulsifying agent purchased from Superior Chemical Company, St. Louis, Mo.) and then biotreated with BNL-4-24. The results of viscosity and emulsification testing of these samples are shown in Table 12.

TABLE 12

| BNL-4-24 Treatment of Pre-emulsified Wilmington Crude Oil | | | |
|---|---|---|---|
| Microorganism | Days incubated | Viscosity at the end of biotreatment in cps | Emulsion in Klett units |
| BNL-4-24 + 0.1% oil + 1% "TERGITOL" | 7 | 2.79 | 7400 |
| BNL-4-24 + 0.1% oil + 0.5% "TERGITOL" | 7 | 3.83 | 8000 |

Figure 38:
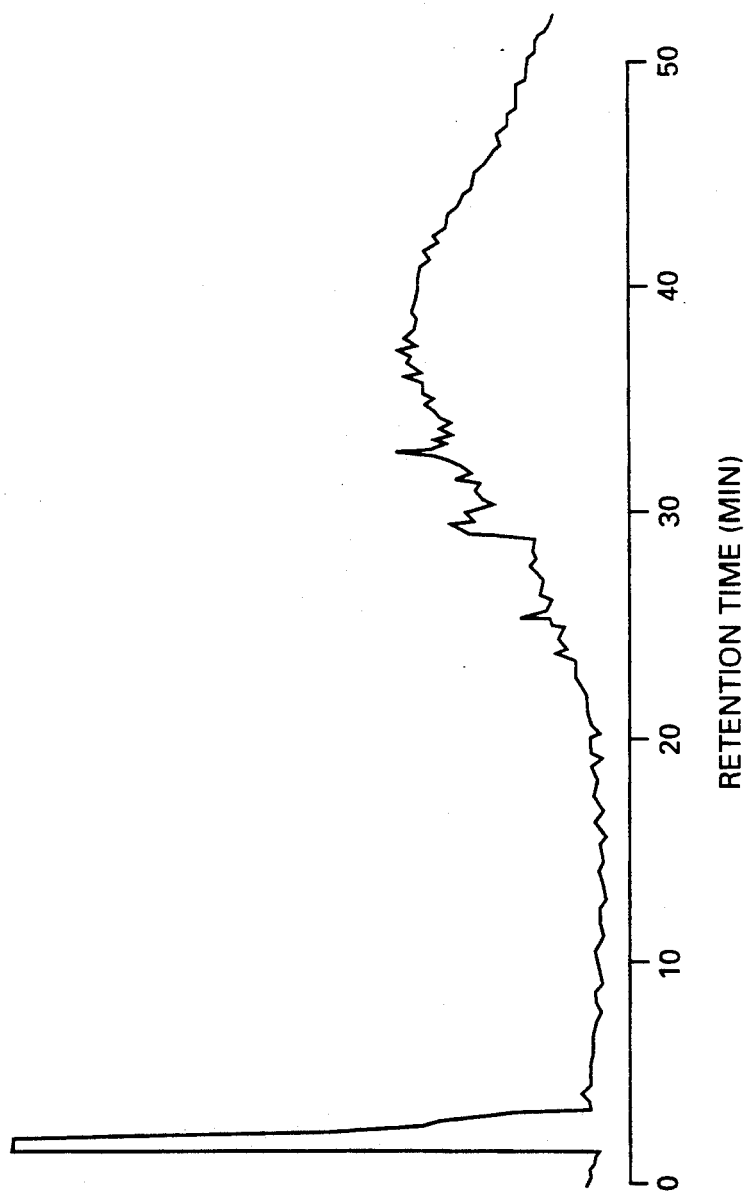
FIG. 38 is a GCFPD trace of Wilmington, Calif., crude pre-emulsified, with 1% Tergitol and Biotreated with BNL-4-24.
Figure 39:
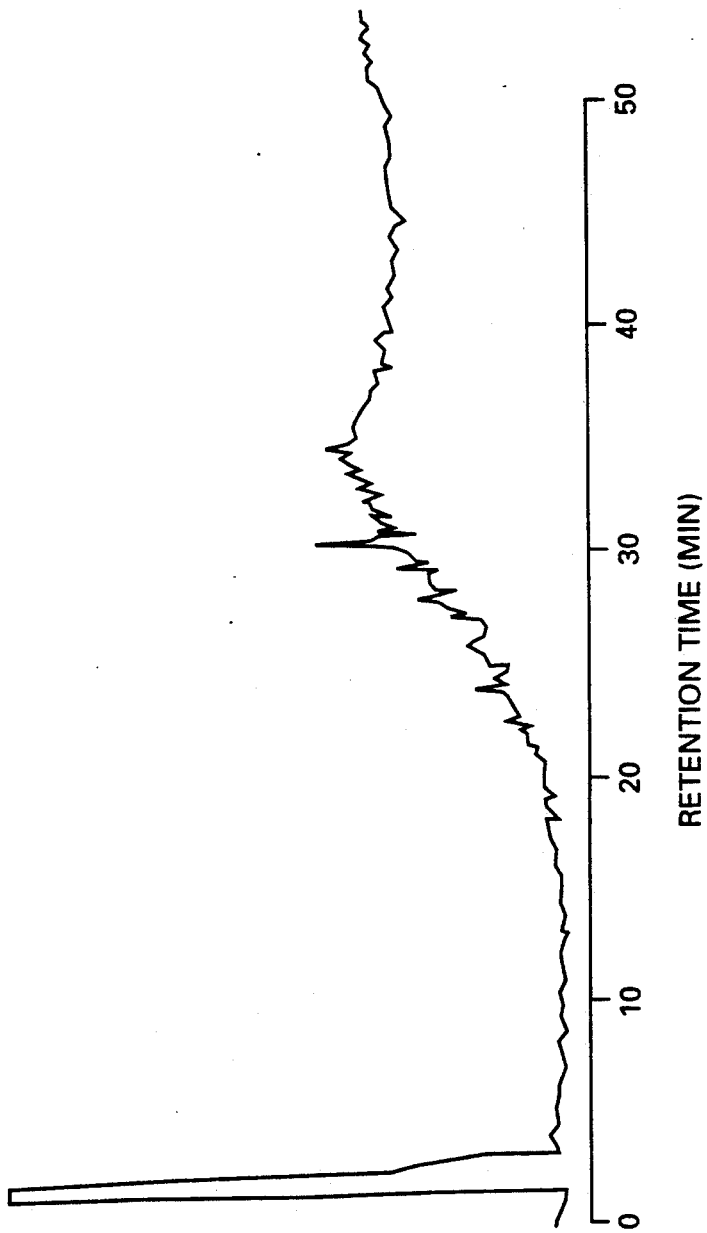
FIG. 39 is a GCFPD trace of Wilmington, Calif., crude pre-emulsified with 0.5% Tergitol and Biotreated with BNL-4-24.

In addition, the samples were tested for their ability to remove sulfur compounds and the results of a GCFPD trace of these samples are shown in FIGS. 38 and 39, respectively. As shown in FIGS. 38 and 39 emulsification of the crude oil even over a much shorter period of time, Seven (7) days in this Example (see Table 12) as compared to 20-30 days in Example 16 (see Table 11), results in considerable enhancement of the effects observed in the biotreatment of crude oil in removing organic sulfur compounds.

Similar experiments have been carried out with Boscan and Cerro Negro oils. The results shown in Table 13 indicate that pre-emulsification causes considerable enhancement of the biotreatment process.

TABLE 13

| Biotreatment of Pre-emulsified Crude Oils | | | | |
|---|---|---|---|---|
| Oil | Microorganisms | Media* | Treatment** | Emulsion in Klett units |
| Boscan | BNL-4-22 | N.B. (10% C) | 0 | 210 |
| | BNL-4-33 | N.B. (10% C) | 0 | 140 |
| | 0 | Control | 0 | 5 |
| Cerro Negro | BNL-4-22 | N.B. (10% C) | 0 | 120 |
| | BNL-4-33 | N.B. (10% C) | 0 | 145 |
| | 0 | Control | 0 | 25 |
| Boscan | BNL-4-22 | Mod (No. C) | Emulsified | 6000 |
| | BNL-4-23 | Mod (No. C) | Emulsified | 5500 |
| | 0 | Control (Oil only) | Emulsified | 2800 |
| | BNL-4-22,23 | Control (Bacteria) | Emulsified | 2600 |

TABLE 13-continued

| Biotreatment of Pre-emulsified Crude Oils | | | | |
|---|---|---|---|---|
| Oil | Microorganisms | Media* | Treatment** | Emulsion in Klett units |
| Cerro Negro | BNL-4-22 | Mod (No. C) | Emulsified | 3800 |
| | BNL-4-23 | Mod (No. C) | Emulsified | 4800 |
| | 0 | Control (Oil only) | Emulsified | 2800 |
| | BNL-4-22,23 | Control (Bacteria Only) | Emulsified | 2600 |

*Nutrient (10% C) added; **"0" means that the organisms were grown under conditions in which the organism generated the emulsification process in the medium. "Emulsified" means that the oil was pre-emulsified and then biotreated. The resulting emulsion is the "cumulative result of pre-emulsification and emulsification generated by the microorganism.

Thus, while we have described what are the preferred embodiments of the present invention, further changes and modifications may be made by those skilled in the art without departing from the scope of the invention, and it is contemplated to claim all such changes and modifications.

We claim:

1. A process for the recovery of oil from an underground oil bearing reservoir comprising:
   injecting into said reservoir an aqueous solution containing a microorganism or a mixture of microorganisms, modified through challenge growth processes to be suitable for microbial enhanced oil recovery said challenge growth processes including:
   (a) selecting a thermophilic microorganism or mixture of thermophilic microorganisms,
   (b) growing said thermophilic microorganism or a mixture of microorganisms in a medium containing crude oil and nutrients, step wise removing up to 90 percent of said nutrients while maintaining growth of said microorganism or mixture of microorganisms in the presence of said crude oil,
   (c) adapting said microorganism or mixture of said microorganisms to a desired reservoir temperature of from about 4° C. to about 85° C.,
   (d) increasing the pressure at which said microorganisms are grown to a desired pressure of from about 200 psi up to about 2,500 psi; and
   (e) growing said modified organisms to their maximum strength and maturity and subsequently removing biotreated oil from the reservoir.

2. The process of claim 1, further comprising injecting a drive fluid into said oil bearing reservoir.

3. The process of claim 1 wherein the modified microorganism is selected from the group consisting of Achromobacter sp. BNL-4-23 (ATCC 55021), Sulfalobus solfataricus BNL-TH-29 (ATCC 55022), Sulfalobus solfataricus BNL-TH-31 (ATCC 55023), Sulfalobus acidocaldarius BNL-TH-1, Pseudomonas sp. BNL-4-24 (ATCC 55024), Leptospirillum ferrooxidans BNL-5-30 (ATCC 53992), Leptospirillum ferrooxidans BNL-5-31 (ATCC 53993), Acinetobacter calcoaceticus BNL-4-21 (ATCC 53996), Arthrobacter sp. BNL-4-22 (ATCC 53997), and mixtures thereof.

4. The process of claim 3, further comprising introducing an emulsifying agent into said oil bearing reservoir prior to or at the time of injection of said aqueous solution containing said microorganism or mixture of microorganisms.

5. The process of claim 1, further comprising introducing an emulsifying agent into said oil bearing reservoir prior to or at the time of injection of said aqueous solution containing said microorganism or mixture of microorganisms.

* * * * *